US005157019A

United States Patent [19]

Glover et al.

[11] Patent Number: 5,157,019

[45] Date of Patent: Oct. 20, 1992

[54] SERINE PROTEASE INHIBITORS

[75] Inventors: George I. Glover, Creve Coeur; Charles S. Schasteen, University City, both of Mo.

[73] Assignee: Monsanto Company, St. Louis, Mo.

[21] Appl. No.: 728,002

[22] Filed: Jul. 1, 1991

Related U.S. Application Data

[63] Continuation of Ser. No. 200,821, Jun. 1, 1988, abandoned, which is a continuation of Ser. No. 6,725, Feb. 6, 1987, abandoned, which is a continuation-in-part of Ser. No. 840,810, Mar. 18, 1986, abandoned.

[51] Int. Cl.[5] .................... A61K 37/02; A61K 37/64; C07K 7/10; C07K 7/08

[52] U.S. Cl. .................................... 514/12; 514/13; 514/14; 514/15; 530/324; 530/325; 530/326; 530/327

[58] Field of Search .............. 530/324, 325, 326, 327; 514/12, 13, 14, 15

[56] References Cited

U.S. PATENT DOCUMENTS 4,455,290 6/1984 Olexa et al. ......................... 530/324
4,485,100 11/1984 Hochstrasser et al. ............ 530/324

OTHER PUBLICATIONS

Chandra et al., Biochemical and Biophysical Research Communications, vol. 103, No. 2, pp. 751-758 (1981).
Chandra et al., Biochemistry, vol. 22, No. 22, pp. 5055-5061 (1983).
Ragg, Nucleic Acids Research, vol. 14, No. 2, pp. 1073-1087, (Jan. 24, 1986).
Carrell et al., Biochemical and Biophysical Research Communications, vol. 91, No. 3, pp. 1032-1037 (1979).
Kurachi et al., Proc. Natl. Acad. Sci. U.S.A., vol. 78, No. 11, pp. 6826-6830 (1981).
Morii et al., The Journal of Biological Chemistry, vol. 258, No. 21, pp. 12749-12752 (1983).
Rudinger, University Park Press, (Parsons ed.), Baltimore, pp. 1-7 (1976).
Carrell et al., *Biochem. and Biophys. Res. Comm.*, 91:1032 (1979).

*Primary Examiner*—Y. Christina Chan
*Attorney, Agent, or Firm*—Dennis A. Bennett

[57] ABSTRACT

Novel peptides which exhibit inhibitory activity toward serine proteases and methods for preparing and using same are disclosed. In one aspect, the present invention provides peptides comprising a generic inhibitory core having a functional site recognition sequence fused to the N-terminus. The functional site recognition sequence is adapted to provide enhanced selectivity and/or potency for a target protease.

25 Claims, 3 Drawing Sheets

SERINE PROTEASE INHIBITORS

This application is a continuation of Ser. No. 200,821, filed Jun. 1, 1988, abandoned, which is a continuation of Ser. No. 006,725, filed Feb. 6, 1987, abandoned which is a continuation-in-part application of co-pending application Ser. No. 840,810, filed Mar. 18, 1986 now abandoned.

BACKGROUND OF THE INVENTION

In its broadest aspect, the present invention, relates to enzyme inhibitors. More particularly, it relates to novel peptides which exhibit inhibitory activity toward serine proteases.

Protease inhibitor activities were first noted in human plasma by Fermi and Pernossi in 1894 Zgcar. Hyg. 18:83). Many investigations have been made to determine the various inhibitory activities present in plasma primarily by adding proteases of varying specificities and catalytic mechanisms to plasma. There are now recognized at least nine separate, well-characterized proteins in human plasma which share the ability to inhibit the activity of various proteases.

Several of the inhibitors have been grouped together, namely α-1-proteinase inhibitor, antithrombin III, antichymotrypsin, C1-inhibitor and α-2-antiplasmin. These are referred to as the α-1-proteinase inhibitor class. The protein α-2-macroglobulin inhibits members of all four catalytic classes: serine, cysteine, aspartic, and metalloproteases. However, the other types of protease inhibitors are class specific. The α-1-proteinase inhibitor group and inter-α-trypsin inhibitor inhibit only serine proteases, α-1-cysteine protease inhibitor inhibits only cysteine proteases, and α-1-anticollagenase inhibits only collagenolytic enzymes of the metalloenzyme class.

α-1-Proteinase inhibitor (antitrypsin, AT) is a glycoprotein of MW 51,000 with 394 amino acids and 3 oligosaccharide side chains and is present in human serum at 130 mg/100 ml or 23.6 μM. It easily diffuses into tissue spaces and forms a 1:1 complex with a target protease, principally neutrophil elastase. The enzyme/inhibitor complex is then removed from circulation and catabolized by the liver and spleen. Human AT was originally named anti-trypsin because of its ability to inactivate pancreatic trypsin. Interest has focused on AT in both clinical and biochemical circles because many individuals with circulating levels of this inhibitor that are less than 15% of normal are susceptible to the development of lung disease (familial emphysema) at an early age (Eriksson (1965) *Acta Med. Scan.* 177 (Suppl. 432): 1-85). Therefore, it appears that this inhibitor represents an important part of the defense mechanism of the lung towards attack by proteases. Human AT is a single polypeptide chain with no internal disulfide bonds and only a single cysteine residue normally intermolecularly disulfide-linked to either cysteine or glutathione.

An important observation is that the reactive site of AT contains a methionine residue which is labile to oxidation. This oxidation to the corresponding sulfoxide which may be caused by cigarette smoke reduces the inhibitory activity of AT toward both pancreatic and neutrophil elastase. Inactive AT isolated from rheumatoid synovial fluid contains up to four methionine sulfoxide residues, two of which are at the P1 and P8 positions suggesting a connection to the tissue damage noted in this disease.

Human antithrombin III (AT III) is a serum glycoprotein (serum level=29 mg/100 mL or 4.7 μM) that plays a major role in controlling serine proteases in the coagulation cascade scheme. Purified AT III is a single-chain molecule of MW 58,000 containing about 15% carbohydrate, and has six disulfide bonds. The major heparin binding site in AT III is in the N-terminus (PNAS (1984) 81, 289-293). The inactivation of proteases by AT III is enhanced 100 fold by the presence of heparin, an effect caused by the increase in binding to the protease.

Antichymotrypsin (ACT) is a plasma glycoprotein of MW 68,000 first isolated and characterized without knowledge of its function (Naturwissenschaften (1962) 49:133). It has since been shown to have inhibitory activity towards chymotrypsin, although its physiological role is thought to be the inhibition of leukocyte cathepsin G. This inhibition is brought about by formation of a 1:1 complex. This inhibitor is an acute phase protein, meaning that its concentration increases dramatically after traumatic events, e.g., surgery, burns, ulcerative colitis, and some cancers. The normal concentration of ACT in plasma is 25 mg/100 mL or 3.6 μM.

It is known that in some instances the degradative action of serine proteases results in serious pathological conditions or disease states. For example, elastase is a protease which causes degradation and fragmentation of elastic fibers as a result of its protelytic activity on elastin the structural component of elastic fiber. Elastic tissue is rich in elastin and possesses a rubber-like property. Cartilaginous tissues present in the ear and epiglottis are considered elastic tissue. Tissue comprising the lungs, bronchi and skin also contain relatively large amounts of elastin and are considered elastic tissue. Elastase is required for turnover of damaged cells and the digestion of certain invading bacteria. However, excessive degradation of elastin has been associated with arthritis, atherosclerosis, certain skin diseases, pulmonary emphysema and adult respiratory-distress syndrome. Therefore, by inhibiting the activity of elastase it is possible to treat a wide variety of pathological conditions.

Proteases serve another important function in human physiology by mediating the activation of the complement system. The complement system consists of a complex group of proteins in body fluids which, working together with antibodies and other factors, play an important role as mediators of inflammation and defense against infections. The complement system is now understood to be composed of two distinct pathways, the "classical" pathway and the "alternative" pathway.

The classical pathway (CP) of complement activation is typically initiated by the union of antigen and antibody. Not all antigen-antibody reactions initiate the classical pathway. Immunoglobulins of the IgM class and IgG1, IgG2, or IgG3 subclass activate the classical pathway whereas IgG4, IgA, IgD and IgE do not. A conformational change presumably occurs after antigen binding to the Fab region of immunoglobulins that permits binding and activation of the first component of complement, C1. C1 is a macromolecular complex of three proteins (C1q, C1r and C1s), and requires calcium ions for both stability and reactivity. Binding of C1 to a suitably altered immunoglobulin leads first to a conformational change in the C1q subunit and later to the acquisition of enzymatic activity by the C1s subunit. Activated C1 (C1s), while bound to antibody, cleaves its natural substrates, C4 and C2, by limited proteolytic reactions. The activity of C1s is regulated by the endogenous serum protein, C1 esterase inhibitor (C1-inhibitor) which binds to the enzyme and thereby limits cleavage of C4 and C2. An inherited deficiency of C1-inhibitor results in uncontrolled cleavage of C4 and C2 and is manifested by recurrent attacks of angioedema (periodically recurring episodes of swelling of skin, mucous membranes, viscera and brain). C4 cleavage by C1s results in the formation of a small peptide (C4a) which is released in the fluid phase and a larger fragment, C4b, which can bind to the immune complex.

C2 is similarly cleaved by C1s into a small peptide (C2b) which is released into the fluid phase and a large fragment (C2a), which binds to C4b. The C4b2a complex thus formed possesses new proteolytic activity (C3 convertase) that is capable of cleaving the third component of complement, C3. Proteolytic cleavage of C3 by the C4b2a complex yields a small peptide, C3a, which is released into the fluid phase and a larger fragment (C3b), which possesses the ability to bind to immune complexes as well as to a variety of surfaces. Once bound, C3b forms a new C4b2a3b complex with surrounding C4b2a complexes, or C5 convertase, which is capable of cleaving native C5 to a small peptide C5a which is released to the fluid phase, and C5b which binds to the surface of the antigen. Bound C5b forms the basis for the stable macromolecular "membrane attack" complex with C6, C7, and C8. Binding of the final complement component C9 forms the attack sequence C5b6789 which inserts into the lipid bilayers of cell membranes and forms transmembrane channels that permit bidirectional flow of ions. This mechanism induces cellular injury and lysis.

The alternative pathway (AP) of complement activation is functionally a two-phase system in which six proteins participate. This pathway bypasses the early-acting components, C1, C4 and C2 and leads directly to proteolytic cleavage of C3 and ultimately to the assembly of the terminal attack complex, C5b–C9. The first phase is initiation in which particle-bound C3b fulfills a recognition function. The second phase is one of amplification by means of a positive feedback loop involving bound C3b, Factor B, Factor D, and unbound C3.

The alternative pathway can be activated by the introduction of a wide variety of substances into serum. These include lipopolysaccharides (e.g., bacterial endotoxins), complex polysaccharides (e.g. inulin, zymosan), and immune complexes containing immunoglobulins of the IgA or IgD classes that cannot activate the classical pathway. Surface constituents of some intact cells (e.g. rabbit erythrocytes, certain bacteria and fungi) activate the alternative complement pathway in human serum. This property of foreign cells provides a mechanism for their recognition in the complete absence of antibody. The alternative pathway may therefore be thought of as a phylogenetically older first line of defense against invading microorganisms. The actual mechanism that activates the alternative complement patyway is controversial because there is no counterpart to the recognition unit C1q of the classical pathway. The current view is that native C3 is undergoing limited proteolytic reactions at all times, i.e. normal catabolism. The C3b fragments formed transiently must be near enough to a suitable surface to attach before the metastable binding site on the C3b molecule decays. The regulatory proteins of the alternative pathway are Factor H and Factor I. Factor H controls the alternative pathway by directly binding to C3b or to the C3bBb complex. When bound to C3b it blocks the formation of the C3bBb complex and when bound to previously existing C3bBb complex it dissociates Bb from the complex. Factor I functions as an endopeptidase cleaving C3b which is complexed with Factor H. C3b which escapes Factor H and binds to a suitable surface can interact with Factor B to form a stable, catalytically inactive bimolecular complex C3bB. This complex, if it escapes from inactivation by Factor H and I, is the precursor of both the C3 and C5 convertases of the alternative pathway. Factor B, when complexed with C3b, becomes susceptible to cleavage by Factor D.

Factor D is not consumed and can activate many C3bBb complexes. The activated C3bBb complex produced is the alternative pathway C3 convertase and is able to cleave free C3 to produce more C3b, which in turn can combine with more Factor B. This positive feedback loop is the central theme of the alternative pathway. Because of this mechanism, deposition of very few molecules of C3b on a biological particle can lead to the subsequent placement of many more molecules of C3bBb on the surface. This results in the opsonization (engulfment) of the particle facilitating its clearance by phagocytic cells and the generation of C3a which functions in the inflammatory process. C3bBb which has been activated by Factor D can be protected from inactivation activity of Factor H by addition of properdin (Factor P) which stabilizes the alternative pathway C3 convertase about eight-fold at 37° C. As the amplification phase continues, the C3bBbP complex binds one additional molecule of C3b, forming C3bBbPC3b, which can cleave C5, producing C5a and C5b. Generation of C5b and its binding to the surface of the particle results in the self assembly of the membrane attack complex C5b-9.

As with nearly all complex physiological pathways, there are situations in which activation of complement is triggered to the detriment of the host. This type of activation often results in grave pathological conditions. Exemplary of these conditions are autoimmune hemolytic anemia, rheumatoid arthritis, allergy complement activation, systemic lupus erythematosus, ankylosing spondylitis and myasthenia gravis. The presence of conditions such as those described above, provokes a much recognized and as yet unmet need for synthetic serine protease inhibitors for use as therapeutic agents.

It should be understood that the pathways and conditions noted above are only exemplary and the present invention is not limited to these states. Rather, the serine protease inhibitors of this invention have broad application in the inhibition of serine protease activity.

Accordingly, it is therefore the overall object of the present invention to provide novel peptides which exhibit inhibitory activity toward serine proteases.

It is an object of the present invention to provide serine protease inhibitors exhibiting relatively high activity at relatively low concentrations.

It is another object of the present invention to provide serine protease inhibitors exhibiting selectivity for certain key proteases involved in complement activation.

It is yet another object of the present invention to provide serine protease inhibitors exhibiting selectivity for certain key proteases involved in blood clotting and clot degradation.

These and other objects and advantages of the present invention will be recognized by those skilled in the art from the following description and illustrative examples.

DESCRIPTION OF THE INVENTION

Figure 1:
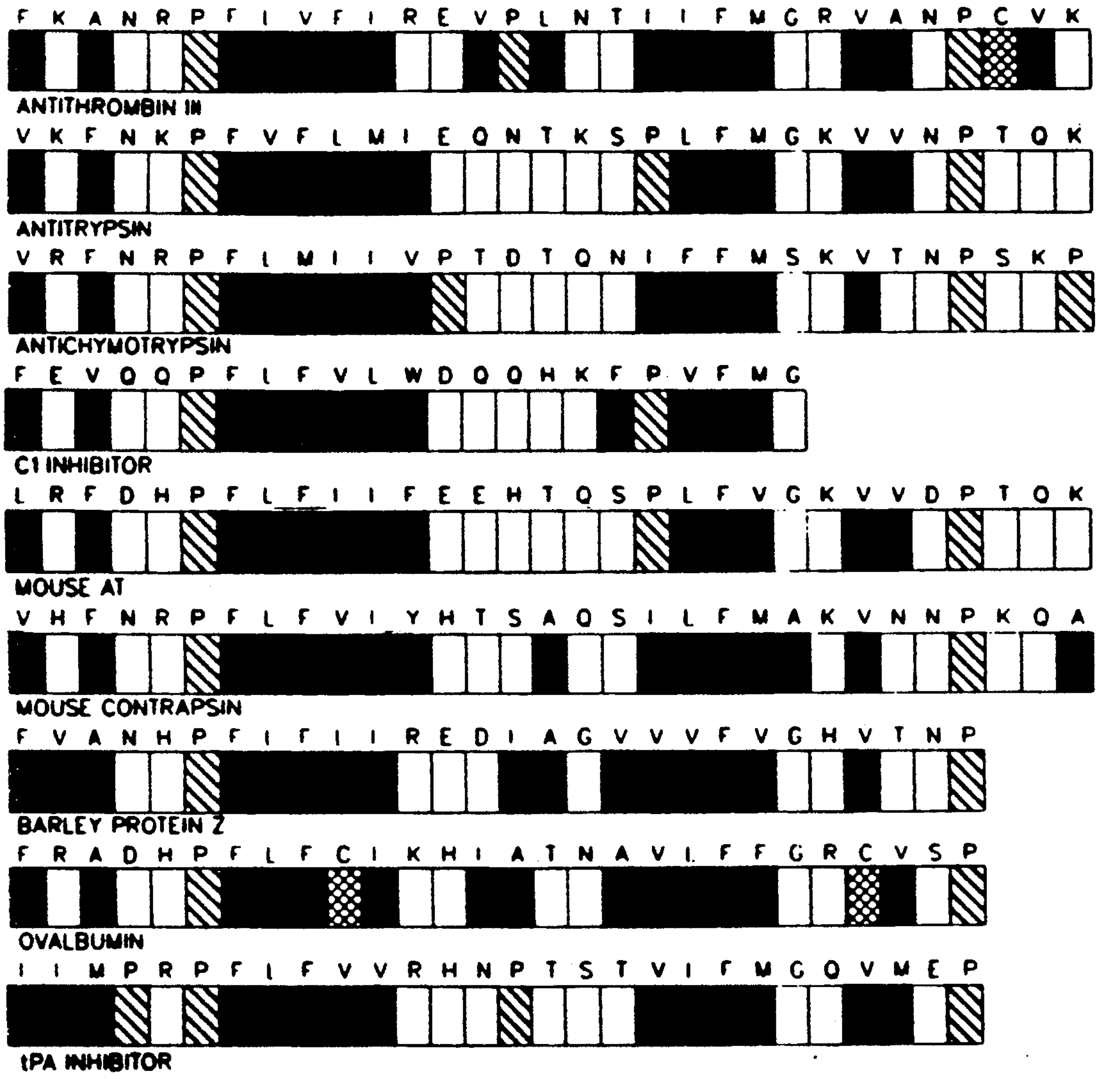
FIG. 1 illustrates the homology which exists between the C-terminal regions of naturally-occurring serine protease inhibitors.

The present invention provides novel peptides which exhibit inhibitory activity toward serine proteases and a method for preparing same. More particularly, the inhibitory peptides comprise a generic inhibitory core sequence comprising between about eleven and thirty-one amino acid residues. In many cases an inhibitory core sequence exhibits inhibitory activity toward a plurality of serine proteases although some selectivity for a particular protease may be exhibited by some species. In a particularly preferred embodiment a suitable functional site recognition sequence is optionally fused to an inhibitory core sequence which is adapted to impart selectivity for a particular serine protease while in some cases increasing the inhibitory potency of the generic inhibitory core sequence.

All peptide structures represented in the following description and claims are shown in conventional format wherein the amino group at the N-terminus appears to the left and the carboxyl group at the C-terminus at the right. Likewise, amino acid nomenclature for the naturally occurring amino acids found in protein and comprising the peptide inhibitors of the present invention is as follows: alanine (Ala;A), asparagine (Asn;N), aspartic acid (Asp;D), arginine (Arg;R), cysteine (Cys;C), glutamic acid (Glu;E), glutamine (Gln;Q), glycine (Gly;G), histidine (His;H), isoleucine (Ile;I), leucine (Leu;L), lysine (Lys;K), methionine (Met;M), phenylalanine (Phe;F), proline (Pro;P), serine (Ser;S), threonine (Thr;T), tryptophan (Trp;W), tyrosine (Tyr;Y), and valine (Val;V).

In the broadest sense the naturally-occurring amino acids can be divided into groups based upon the chemical characteristic of the side chain of the respective amino acids. By "hydrophobic" amino acid is meant either Ile, Leu, Met, Phe, Trp, Tyr, Val, Ala, Cys or Pro. By "hydrophilic" amino acid is meant either Gly, Asn, Gln, Ser, Thr, Asp, Glu, Lys, Arg or His. This grouping of amino acids can be further subclassed as follows. By "uncharged hydrophilic" amino acid is meant either Ser, Thr, Asn or Gln. By "acidic" amino acid is meant either Glu or Asp. By "basic" amino acid is meant either Lys, Arg or His.

A new protein super family was proposed by Hunt and Dayhoff (*Biochem. Biopys. Res. Comun.* (1980) 95:864–71) on the basis of the amino acid sequence homology between chicken ovalbumin and, AT III and AT, two plasma serine protease inhibitors which appeared to be homologous to one another (Carrell et al. *Biochem Biophys. Res. Commun.*, (1979), 91:1032–7). The complete amino acid sequences of AT III (Chandra et al. *Biochem.* Biophys. Res. Commun., (1981) 103751–8); AT (Kurachi et al. Proc. Nat. Acad. Sci., (1981) 78:6826–30); and ACT (Chandra et al. Biochem. (1983) 22:5055–61) have been reported. A comparison of the amino acid sequence homology between ACT and AT or AT III indicated overall homology of 42% and 33% respectively (Chandra et al. Biochem (1983) 22: 5055–61). A further conclusion was that ACT is significantly more homologous to AT than it is to AT III. Also, there appeared to be more sequence homology between the N-terminal halves of ACT and AT than between the C-terminal halves. A further comparison of amino acid sequences around the reactive sites, which are the sites where the protease inhibitors are cleaved by the proteases during the inactivation of the proteases by complexation with the inhibitors, suggested that the homologies were much less extensive and that the homologies appear to resume about 5–10 residues away from the cleavage site. A separate comparison of the amino acid sequences of the reactive sites of AT and AT III indicated a great deal of homology (Morii & Travis, *J. Biol. Chem.*, (1983) 258:12749–52).

Those skilled in the art recognize that the degree of homology found in amino acid sequence comparisons depends on the basis on which sequences are compared. Generally the assumption is made that there is an ongoing process of mutation that tends to cause proteins derived from a common ancestral protein to have divergent sequences and therefore less and less sequence homology with time. Two accepted mutational events are single base changes in codons changing the amino acid encoded therein and deletions of one or more codons corresponding to deletion of one or more amino acids (Dayhoff, Barker & Hunt, *Methods in Enzymol.*,(1983) 91:524–45). Generally sequences are compared looking for identical matches between them. Gaps are introduced to maximize matches. The length of the sequences compared and the criteria for matches can account for discrepancies in the perceived degree of homology.

Given that a protein superfamily appears to exist which includes mammalian protease inhibitors, one would like to be able to identify functional regions of the proteins on the basis of amino acid sequence comparisons. It is assumed that within the tertiary structure of a molecule there is likely to be secondary structural elements which are essential for the function of the protein. While at present there are no general methods to reliably predict essential secondary structural elements, one may assume that relatively invariant secondary structures are likely to have relatively invariant primary structures. More specifically, it is reasonable to assume that there are similar secondary structural elements in the various plasma protease inhibitors that are essential for binding to proteases. The problem is discovering a basis for defining and identifying relatively invariant primary sequences that actually represent functional secondary structural elements. This was accomplished in the present invention by use of a somewhat different basis for comparing amino acid sequences as described hereinafter.

Sequence homology was determined for the C-terminal end of AT, AT III, ACT, C1-inhibitor, tPA-inhibitor, mouse AT, mouse contrapsin, as well as for the C-termini of barley protein Z, and ovalbumin. While the functions of barley protein Z and ovalbumin are unknown, it has been speculated that ovalbumin and barley protein Z may be primordial protease inhibitors. Homology was determined by looking for similar patterns of amino acid sequence while not permitting deletions and/or gaps as comparisons were made. Amino acids having chemically similar side-chains should, in most cases, promote similar-type secondary structure. Hence, for purposes of sequence comparison for one embodiment of the present invention, Ile, Leu, Met, Phe, Trp, Tyr, Val or Ala having hydrophobic side chains are considered functionally identical; and Gly, Asn, Arg, Gln, Ser, Thr, Asp, Glu, Lys or His having hydrophilic side-chains are considered functionally identical. Pro is hydrophobic but is distinguished since it is known to disrupt local secondary structure and appears relatively invariant in the naturally occurring protease inhibitors listed above. Although considered hydrophobic, Cys is also distinguished since it is known to impart structural constraints on an amino acid sequence by forming disulfide bonds with other Cys residues.

The present invention also embraces in another aspect a method for preparing novel serine protease inhibitors based, in part, on the homologous C-terminal portions of naturally-occurring serine protease inhibitors and other homologous protein sequences. Referring to FIG. 1, there is shown a block diagram illustrating the homology of the C-termini of human Antitrypsin (AT), Antitrombin (ATIII), Antichymotrypsin (ACT), C1-inhibitor, tPA-inhibitor, mouse AT, mouse contrapsin, barley protein Z, and ovalbumin. Black blocks represent hydrophobic amino acid residues and white blocks represent hydrophilic amino acid residues.

For purposes of the present invention, the term "R" represents an amino acid residue naturally occurring in protein. The relative position for each amino acid residue is denoted by an integer subscript, the values of which increase from the N-terminus to C-terminus of the subject peptide or protein. A subject peptide region (for example, region $R_{x-y}$) is considered "substantially hydrophilic" if over half of the amino acids comprising the subject region are hydrophilic amino acid residues. Conversely, a region is "substantially hydrophobic" if over half of the amino acids comprising the subject region are hydrophobic. As can be seen in the patterns shown in FIG. 1, these sequences are surprisingly homologous. It was further found that region $R_{12-19}$ can be quite variable (see Example 2 and discussion below).

Hence, the present invention embraces, in one aspect, a generic serine protease inhibitor sequence having the following structure:

$$R_{1-5}\text{-Pro-}R_{7-11}\text{-}R_{12-19}\text{-}R_{20-27}\text{-Pro-}R_{29-31} \qquad \text{(I)}$$

in which each R is an amino acid residue; $R_{1-5}$ is a substantially hydrophilic region; $R_{7-11}$ is a substantially hydrophobic region; $R_{12-19}$ is a region containing hydrophobic residues, hydrophilic residues or mixtures thereof and is preferably adapted to provide a turn thereby causing the peptide to fold back on itself $R_{20-27}$ is a substantially hydrophobic region and $R_{29-31}$ is a substantially hydrophilic region. It is believed that homologous variations of the peptides embraced by structure I are also serine protease inhibitors and therefore are considered to be within the scope of this invention.

Figure 2:
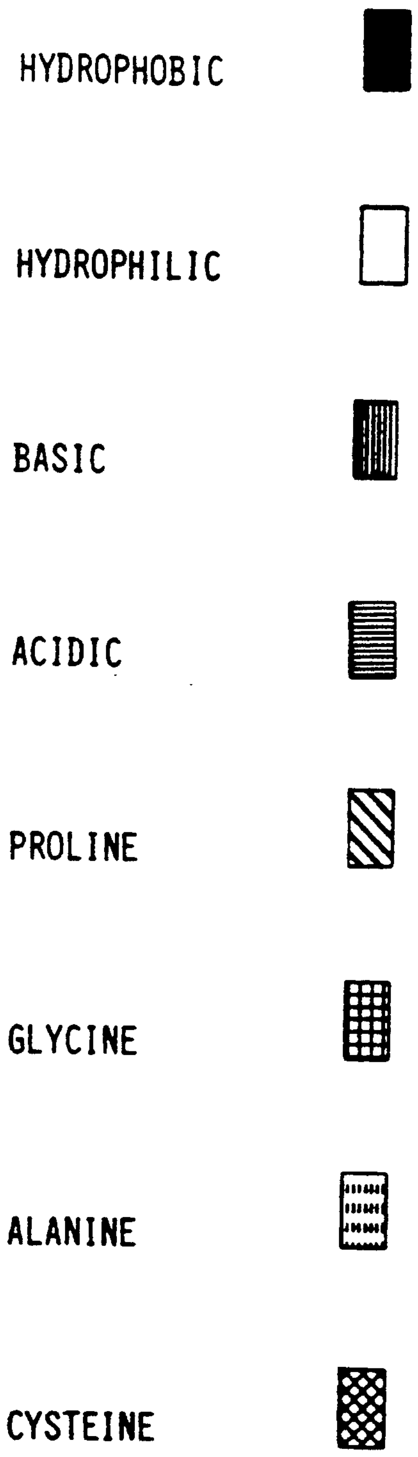
FIG. 2 illustrates the functional identity criteria used for the homology comparison of FIG. 3.
Figure 3:
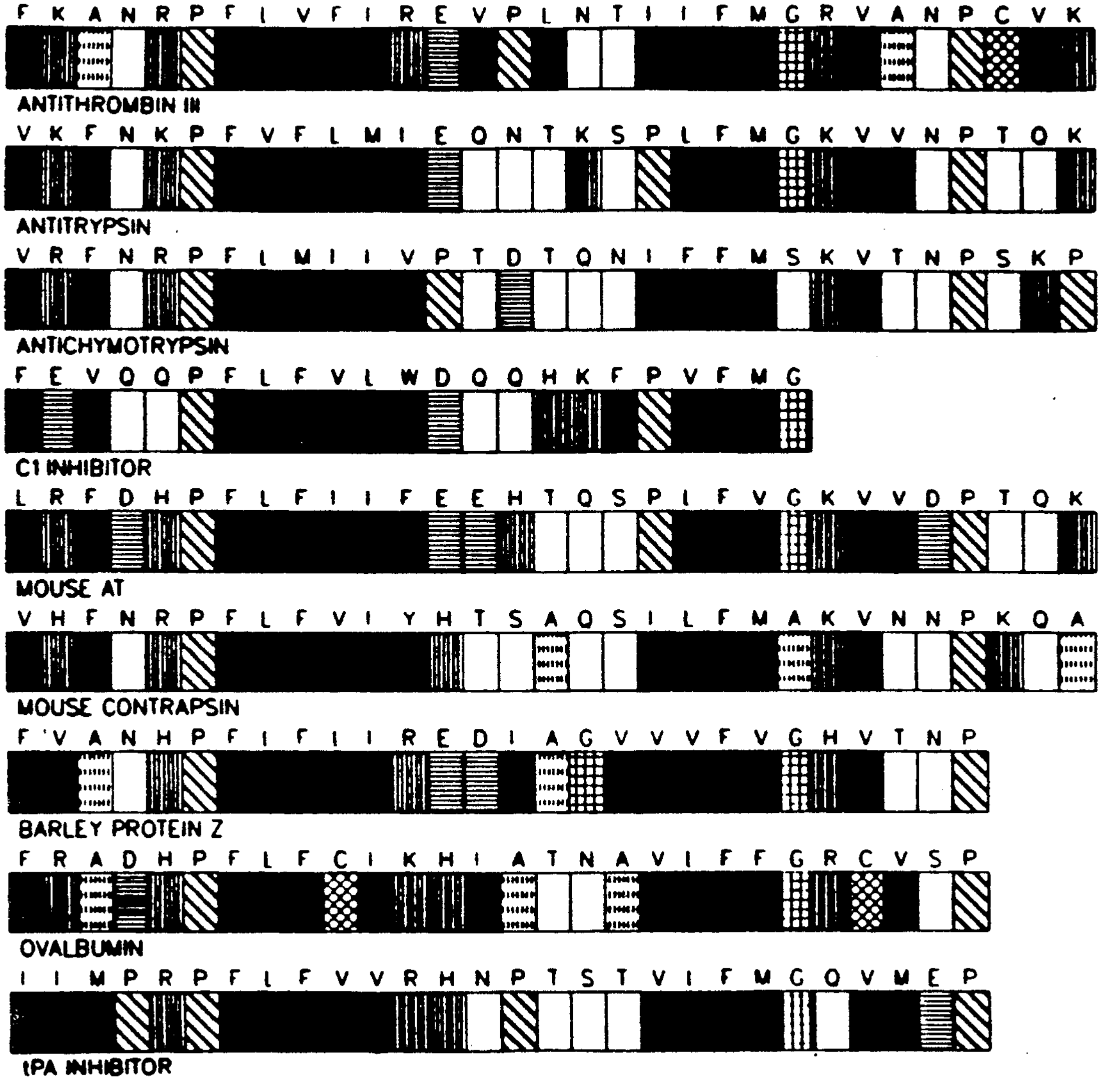
FIG. 3 illustrates the homology which exists between the C-terminal regions of naturally-occurring serine protease inhibitors using the functional identity criteria shown in FIG. 2.

In another aspect, the present invention embraces the homology shown in FIG. 3. For purposes of the homology comparison of FIG. 3, the amino acids Tyr, Trp, Phe, Leu, Ile, Met, and Val having hydrophobic side chains are considered functionally identical; Lys, Arg and His having basic side chains are considered functionally identical; Glu and Asp having acidic side chains are considered functionally identical; and Gln, Asn, Thr, and Ser having uncharged hydrophilic side chains are considered functionally identical. Even though it is hydrophobic, proline is again distinguished due to its effect on local secondary structure. Gly, although marginally hydrophilic, is distinguished since it has no side chain. Ala, although marginally hydrophobic, is distinguished since it has a small side chain. The Cys residues, although considered hydrophobic, were distinguished for their constraints on structure due to potential disulfide bond formation. However, it should be understood that the general use of cysteine residues as hydrophobic amino acid residues in the peptides of this invention is only restricted in the sense that they do not form disulfide bonds which would unduly diminish the activity of the peptide inhibitor. Refer to FIG. 2 for a legend showing the symbolic representation for the amino acid classifications of FIG. 3.

Note that the structurally conserved inhibitory cores of the protease inhibitors of FIG. 3 are not invariant in sequence, but are regions of significant similarity: the hydrophobic residues 1,2 (excepting AT-III), 3–11, 20–22 and 25; the basic residues 2 (excepting C1 inh), 5, 24 and 31 (excepting ACT); the asparagine or glutamine at residues 4 and 27 (excepting mouse AT); and the prolines at residues 6 and 28 make up 19 out of 31 identical or chemically similar residues, equivalent to 61% identity. The variable regions of the long inhibitory core sequences, $R_{12-19}$, are similar in content. Residues 26, 29 and 30 are the only quite variable residues both in terms of sequence and chemical nature. Since the patterns of chemical similarity of residues 12–19, 26, 29, and 30 vary considerably, these sequences may not be functional as far as the proposed generic binding to serine proteases is concerned, as noted above.

Hence, the present invention embraces, in another aspect, a generic serine protease inhibitor sequence having the following structure:

$$R_{1-5}\text{-Pro-}R_{7-11}\text{-}R_{12-19}\text{-}R_{20-27}\text{-Pro-}R_{29-31} \qquad \text{(II)}$$

in which $R_1$, $R_3$, $R_{7-11}$, $R_{19-22}$ and $R_{25}$ are hydrophobic amino acid residues; $R_2$, $R_5$, $R_{24}$ and $R_{31}$ are basic amino acid residues; $R_4$, $R_{26-27}$ and $R_{30}$ are uncharged hydrophilic amino acid residues, and $R_{12-19}$ is a region containing hydrophobic residues, hydrophilic residues or mixtures thereof and is preferably adapted to provide a turn in the tertiary structure thereby causing the peptide to fold back on itself. In one preferred embodiment $R_4$ and $R_{27}$ are asparagine residues and $R_7$ and $R_{21}$ are phenylalanine residues.

In yet another aspect of the present invention, it has been determined that shortened inhibitory core sequences, based on structures I and II described above, also exhibit generalized inhibitory activity toward serine protease. More specifically, in one aspect these shortened inhibitory cores have the following structure:

$$R_{1-5}\text{-Pro-}R_{7-11} \qquad \text{(III)}$$

in which $R_{1-5}$ is a substantially hydrophilic region; and $R_{7-11}$ is a substantially hydrophobic region.

Using the homology criterion described with respect to FIG. 3, the present invention also embraces shortened inhibitory core sequences having the following structure:

$$R_{1-5}\text{-Pro-}R_{7-11} \qquad \text{(IV)}$$

in which $R_1$, $R_3$ and $R_{7-11}$ are hydrophobic amino acids; $R_2$ and $R_5$ are basic amino acid residues and $R_4$ is an uncharged hydrophilic amino acid residue. In another preferred embodiment $R_4$ is an asparagine residue and $R_7$ is a phenylalanine residue.

As will be evident from the above description and following illustrative examples, structures I, II , III and IV define generalized serine protease inhibitors. Any species within the genera described by structures I through IV above, may have inhibitory activity toward a number of serine proteases. Indeed, this cross-activity would be expected in view of the fundamental inhibitory nature of the proteins on which structures I–IV are based. It should be understood however that while a particular species may have cross-activity toward a number of proteases, it is expected that the level of inhibition would not necessarily be constant and that some species may exhibit substantial selectivity for individual serine proteases.

Those skilled in the art will recognize, as stated above, that substantially homologous variations of inhibitory core structures I, II, III or IV described above will also exhibit protease inhibitory activity. Exemplary variations include, but are not necessarily limited to, peptides having insertions, deletions, replacements, additional amino acids on the carboxy-terminus or amino-terminus portions of the subject peptides and mixtures thereof. For example, peptide 37 (shown in Tables I(b) and II(b)) has 7 amino acid residues deleted from the N-terminus of the AT-III inhibitory core (peptide 21). Region $R_{12-19}$ has been shown to be quite variable (Example 2) and may be shortened while still maintaining an active inhibitor. It is also expected that one or more of the proline residues can be shifted or even removed while still maintaining the inhibitory activity. Accordingly, those homologous peptides having inhibitory activity toward serine proteases are considered to be within the scope of this invention. Homology of a subject peptide to those embraced by sequences I–IV may be determined in a variety of ways.

A particularly preferred method for determining the homology between a subject peptide and peptide structure (I) is described by Lipman et al. (*Science,* Mar. 22, 1985, Volume 227, pp 1435–1441), the disclosure of which is hereby specifically incorporated by reference. Of course, the visual recognition of patterns as exemplified in FIGS. 1 and 3 is also a preferred method for determining homology. The generic peptide (peptide 23) has substantial deviation in actual sequence identity while maintaining the overall functional identity described by sequences I and II. Hence, for purposes of the present invention, peptides are considered homologous if the subject peptides have about fifty percent or more homology based on the functional identity algorithm used in the comparison of FIG. 3. Those skilled in the art will recognize that other natural or unnatural (those not naturally-occurring in protein) or synthetic amino acids may be substituted into these peptides when their side chains provide the functional identity needed to maintain sequence homology (as determined by patterns—FIGS. 1 and 3). For example, ornithine is a basic amino acid that may substitute for Lys, Arg or His. $\beta$-2-thienylalanine is a synthetic amino acid which is a phenylalanine analogue and is therefore hydrophobic. Of course, appropriate stereoisomers of the amino acids found normally in proteins or of natural or unnatural amino acids not found in proteins could be substituted, provided the biological activity is not adversely affected.

The peptide inhibitors of the present invention can be chemically modified so that they are irreversible protease inhibitors. This would afford the advantage of permanently inhibiting the enzyme by covalent attachment of the peptide. This could result in lower effective doses and/or the need for less frequent administration of inhibitor.

Appropriate modifications may include, but are not necessarily limited to, halomethyl ketones (Br, Cl, I, F) at the C-terminus, Asp or Glu, or appended to functional side chains; haloacetyl (or other $\alpha$-haloacetyl) groups on amino groups or other functional side chains; epoxide or imine-containing groups on the amino or carboxy termini or on functional side chains; or imidate esters on the amino or carboxy termini or on functional side chains.

This is a unique approach to designing protease inhibitors. Normally comparisons are made between the residues directly at the cleavage site or no more than a few residues preceding and following the site of cleavage of the natural substrates for the proteases. Typically protease inhibitors have been based on the several residues N-terminal to and including the residues at the site of cleavage in substrates. It is therefore unexpected to find that a sequence remote from the cleavage site of protease inhibitors would in fact be a protease binding region. Natural protease inhibitors can be considered substrates since they are cleaved by the proteases in the process of inhibition. In considering protease inhibitors as substrates and attempting to synthesize peptide inhibitors corresponding in sequence to the protease inhibitors, it has been shown that peptides with the same sequence as the cleavage site of some trypsin inhibitors are in fact relatively poor inhibitors (Tan & Kaiser *Biochem.* (1977) 16, 1531–41; Kitchell & Dykes *Biochem Biophys. Acta,* (1982) 701, 149–52.) We have further found that peptide 15 which is the cleavage site sequence of AT III, is not a good protease inhibitor.

In yet another aspect of the present invention it has been found that a functional site recognition sequence can be fused to the N-terminus of inhibitory core sequences I through IV to impart selectivity for a particular serine protease. The functional site recognition sequence is represented by $R_{-x-0}$ denoting amino acid position -x to 0. In some cases, the fusion peptide inhibitor $R_{-x-0}$-$R_{1-31}$ will also exhibit enhanced inhibitory activity.

An effective functional site recognition sequence for a predetermined protease can be determined in various ways. One method is to design the functional site recognition sequence after the cleavage site sequence of the naturally occurring protease inhibitor for the subject protease. Once the sequence is determined at the cleavage site of the naturally-occurring protease inhibitor, a peptide is synthesized which extends several amino acid residues in both directions in the subject sequence. It has been found that useful functional site recognition sequences can often be obtained by copying the naturally-occurring sequence in the carboxy-terminus direction from the cleavage site until a basic amino acid (lysine or arginine) is encountered. Further extension of this peptide to the C-terminus then picks up the inhibitory core structure $R_{1-31}$ or structure $R_{1-11}$. In other cases the cleavage site may have to be more distant or less distant from the core structure I–IV to obtain the desired result described above. The functional site recognition sequence should include an adequate number of amino acid residues on the amino-terminus side of the cleavage site to obtain the desired result described above.

While this approach is deemed to be a route to obtaining a useful functional site recognition sequence ($R_{-x-0}$), those skilled in the art will recognize that such a method will not work in all cases. The failure of this method in some cases is not surprising in view of the fact that peptides resembling the cleavage site of naturally-occurring inhibitors may have little affinity for the subject protein. For example, a twenty-eight residue peptide spanning the site of cleavage in complement protein C3 is a poor inhibitor of C3-convertase. Thus, it is not surprising that the peptide sequence resembling the C3 substrate cleavage site is not a good functional site recognition sequence for C3-convertase when fused to the short inhibitory core sequence $R_{1-11}$.

Yet the examples provided below clearly demonstrate that one can direct inhibitors to serine proteases based on this approach. For example, complement protease C1s is inhibited by peptides 14 and 35 containing the substrate cleavage site of C4 (the natural substrate for C1s) as the functional site recognition sequence. This method for determination of useful functional site recognition sequences is further supported by the fact that some of the inhibitors of this invention containing the cleavage site regions of AT-III, AT and ACT attached to any of the three corresponding inhibitory cores yields an inhibitor having essentially the same potency as the peptide which is derived from the naturally-occurring protease inhibitor. Example 7 shows data for peptides containing various functional site recognition sequences from C4. These data support the efficacy of inhibitory peptides prepared as described above.

Peptides containing functional site recognition sequences based on the cleavage site of the α-chain of fibrinogen (peptides 27 and 28) and prothrombin (peptide 34) are effective protease inhibitors although no great selectivity for the target protease is exhibited. As noted above, an explanation for the lack of selectivity enhancement may be that the cleavage site in these candidate functional site recognition sequences may not be properly positioned with respect to the inhibitory core sequence. This can readily be seen when comparing the locations of the cleavage sites in the natural protein with respect to the inhibitory core sequence for AT, AT-III, and ACT. Clearly in the design of substrate cleavage site/inhibitory core fusions one must allow for the uncertainty in where to put the cleavage site by varying the distance of the cleavage site from the inhibitory core sequence. For the purposes of providing illustrative examples, the substrate cleavage region was fused to the inhibitory core at a basic amino acid residue, (Lys or Arg) common to both sequences. It is understood that the utility observed for the functional site recognition sequences derived in this manner can be increased by extending it in the N-terminal direction thereby increasing the homology between the peptide inhibitor and the naturally occurring protein inhibitor.

While the method described above is believed to be the most direct route to obtaining useful functional site recognition sequences, it should be understood that the present invention is not so limited. Indeed, those skilled in the art may determine useful functional site recognition sequences which do not directly resemble the cleavage site sequences of naturally-occurring protein inhibitors. One may obtain useful functional site recognition sequence by screening variations of the sequences based on the above method or other sequences known or found to have an affinity for the functional site of the subject serine protease. For example, peptide 33 which includes a functional site recognition sequence based on the cleavage site of AT-III is a more effective complement inhibitor than the generic inhibitory core sequence as represented by peptide 23. A further example is found in the well-established fact that α-1-proteinase inhibitor, which is an elastase inhibitor, was first named for its inhibition of trypsin, an enzyme with a grossly different specificity than elastase.

The peptides of the present invention are used as therapeutic agents in the treatment of a physiological condition caused in whole or part, by uncontrolled serine protease activity. The peptides may be administered as free peptides or pharmaceutically acceptable salts thereof. The term "pharmaceutically acceptable salt" refers to those acid addition salts or metal complexes of the peptides which do not significantly or adversely affect the therapeutic properties (e.g. efficacy, toxicity, etc.) of the peptides. The peptides should be administered to individuals as a pharmaceutical composition which, in most cases, will comprise the peptide and/or pharmaceutical salts thereof with a pharmaceutically acceptable carrier. The term "pharmaceutically acceptable carrier" refers to those solid and liquid carriers which do not significantly or adversely affect the therapeutic properties of the peptides. The pharmaceutical compositions containing peptides of the present invention may be administered to individuals, particularly humans, either intravenously, subcutaneously, intramuscularly, intranasally or even orally. The necessary dosage will vary with the particular condition being treated, method of administration and rate of clearance of the peptide from the body. In most cases dosages between 0.001 and 30 mg/kg should be effective. A dose range between 0.1 and 10 mg/kg is preferred.

The above-described peptides may be prepared by any suitable synthesis method. Exemplary synthesis methods include solid-phase synthesis techniques as described in the textbook entitled "Solid-Phase Peptide Synthesis", Steward & Young, Freeman & Co., San Francisco (1969), solution synthesis and the fragment condensation synthesis methods. Those skilled in the art of biochemical synthesis will recognize that such synthesis methods require the use of a protecting group to stabilize a labile side chain to prevent the side chain from being chemically altered during the synthesis process. Protection of the alpha-amino group is most commonly required to insure proper peptide bond formation, followed by selective removal of the alpha-amino protecting group to permit subsequent peptide bond formation at that location. In selecting a particular side chain protecting group to be employed in the synthesis of such peptides, the protecting group should be stable to the reagents and conditions employed for removal of the alpha-amino protecting group at each step in the synthesis process and must be removable upon completion of the synthesis process under reaction conditions which will not detrimentally alter the peptide.

For commercial-scale quantitites of peptides, such peptides are preferably prepared using recombinant DNA techniques. If prepared by a synthesis method, the peptides of this invention are preferably prepared using solid phase synthesis, such as described by Merrifield, *J. Am. Chem. Soc.*, 85, p 2149 (1963).

Briefly, the solid-phase synthesis method is based on the premise that amino acids can be assembled into a desired peptide having a predetermined sequence while the carboxyl end of the peptide chain is anchored to an insoluble support. After the predetermined sequence of amino acids has been linked together, the peptide chain can be cleaved from the support thereby releasing the peptide into solution. Utilization of the insoluble support obviates the need for purification of intermediate peptides. Furthermore, the entire peptide synthesis can be carried out in a single vessel eliminating the need to transfer material from one container to another. This method of peptide synthesis is well within the skill of those involved in protein biochemistry.

Typically, the solid support is a synthetic polymer having reactive substituent groups. The support must be fully inert to reagents used in the synthesis process. Most often, the support consists of fine beads of a synthetic resin made by the copolymerization of styrene and 2% divinyl benzene. This polymer consists of relatively long alkyl chains bearing a phenyl substituent on every other carbon atom. The chains are stabilized by crosslinking at about every fiftieth carbon atom using p-diethylbenzene. This low degree of crosslinking yields a resin that swells considerably but is insoluble and inert to solvents utilized in the process. The phenyl groups are chloromethylated in a Friedel-Crafts reaction with chloromethylmethyl ether and stannic chloride to provide attachment sites for the carboxyl-terminus amino acid residue. During this reaction, the amine groups of the amino acid must be blocked with a protecting group, usually a t-butyloxycarbonyl group so that it will not react with the support polymer. The chloromethyl substituent reacts with the salt of the predetermined t-butyloxycarbonyl amino acid to form an ester linkage between the amino acid and the support polymer. The amino protecting group is removed by treatment with anhydrous trifluoroacetic acid in a suitable organic solvent, such as methylene chloride. The aminoacyl resin trifluoroacetate is then neutralized with a solution of tertiary amine to produce a free amine group for coupling with the next amino acid.

A second amino-protected amino acid residue is reacted with the support usually in the presence of a coupling agent such as dicyclohexylcarbodiimide. The amino protected dipeptide resin can be successively deprotected, neutralized and coupled with predetermined amino acids to produce the desired peptide-resin combination.

The peptide can be easily cleaved from the support polymer in the following manner. One gram of peptide-resin is reacted with about 10 ml of liquid hydrogen fluoride and 1 ml of anisole for about 30 minutes at about −15° C. The temperature is raised to about 0° C. and the reaction is allowed to proceed for an additional 30 minutes. For peptides containing cysteine or methionine residues, 2-mercaptopyridine (150 mg/g. peptide-resin) is added as an oxidation scavenger.

Upon completion of the above cleavage reaction, the peptide resin mixture is transferred to a coarse sintered glass filtering apparatus and washed three-times with ethyl ether (total 100 ml) to extract residual hydrogen fluoride and anisole. If 2-mercaptopyridine is used in the cleavage reaction, the resin is also washed five-times with ethyl acetate (total 150 ml). The resin is then washed three-times with 50% acetic acid (total 120 ml). Prior to each acid wash the resin is mixed with the 40 ml acetic acid aliquot for about 5 minutes before filtering. The filtrate containing the dissolved subject peptide is then diluted 1:2 (v/v) with distilled water and lyophilized.

The crude preparation of cleaved peptide is purified in the following manner. Crude peptide (lyophilized preparation) is dissolved in a 60:40 distilled water:acetonitrile solution with 0.1% trifluoroacetic acid at a concentration of about 10 mg peptide/ml solution. Purification is then carried out by high or low pressure liquid chromatography. In each case, pure peptides are resolved by gradient or isocratic elution with acetonitrile. Trifluoroacetic acid (0.1%) is added to all solvents to increase resolution. Purified peptides are made hydrochloride salts by dissolving the subject peptide at a concentration of about 1 mg/ml in 0.05N HCl and lyophilizing. The subject peptide is then dissolved in distilled water and relyophilized to remove excess hydrogen chloride.

Inhibitory activity of the subject peptides can be determined using the assays described below. It should be understood that the protease assays listed below are only exemplary and that the utility of the peptide inhibitors are not limited to the proteases discussed below.

Elastase Assay

Enzyme used is "HUMAN SPUTUM ELASTASE ®" which is an enzyme which is the target protease for α1 antitrypsin from Elastin Products Company, Catalog No. SE563, lot 85071, 875 units/mg as determined by supplier with N-Suc-Ala-Ala-Ala-pNA; prepared at 0.2 mg/mL in 0.1M Tris-HCl, pH 8.8 at 37 degrees C. An amount of enzyme is used to give approximately 0.1 change in Absorbance/min; which in this assay was 1 μg.

The substrate is MeO-Suc-Ala-Pro-Val-pNA, Sigma Catalog No. M-4765. About 50 mg of the substrate is dissolved in 1 ml of 1-methyl-2-pyrrolidinone and diluted to 33 mls. with 0.1M Tris-HCl, pH 7.5, containing 0.5M NaCl, and 0.01 wt % sodium azide.

Peptide solutions are prepared at 500 μM, using 1.5% of the final volume of DMSO first and diluting with distilled water (DW) or 0.1M Tris.HCl, pH 8.8 at 37 degrees C.

$$\% \text{ Inhibition} = 100 \times \frac{\text{Rate}_{control} - \text{Rate}_{inhibitor}}{\text{Rate}_{control}}$$

Cathepsin G Assay

Reference: Elastin Products Company (EPC) technical data sheet, cathepsin G, No. SG-45.

Method: Spectrophotometric rate determination

Conditions: 410 nm, 25° C., pH 7.5

Reagents

A) Buffer; 0.1M Tris, pH 7.5 at 25° C.

B) Substrate; 60 mM Suc-Ala-Ala-Pro-Phe-pNA obtained from Sigma Chemical Company. Solution prepared by dissolving 50 mg substrate in 1.3 ml of 1-methyl-2-pyrrolidinone. Stored at 5° C.

C) Peptide Inhibitors; 200 μM HCl salt. Depending on peptide solubility, dissolved in buffer or DMSO and then buffer added for a final concentration of 10% DMSO.

D) Enzyme; Cathepsin G. EPC SG-45, lot 85117 used for all assays, 0.0077 mg protein per mg solid determined by supplier by Bradford method. Enzyme was dissolved in buffer at a concentration of approx. 5 mg/ml solid. Solution stored on ice, used within 2 hours.

Procedure

Pipetted the following into semi-micro quartz cuvettes: 0.3 ml buffer, 0.15 ml peptide solution and 0.5 ml of substrate solution. Equilibrate for 5 min. at 25° C., then add 0.05 ml of enzyme solution and monitor the release of pNA spectrophotometrically at 410 nm for at least 3 minutes. The controls contain either 0.45 ml of buffer or 20% DMSO in buffer (for a final concentration of 10% DMSO).

The rate (O.D./min) is obtained as an average over 3 minutes.

$$\%\ \text{Inhibition} = \frac{\text{Rate}_{control} - \text{Rate}_{inhibitor}}{\text{Rate}_{control}} \times 100$$

Hemolytic Assay

METHOD: Complement activation of the classical and alternative pathways is measured by lysis of EA and ER cells (respectively) after incubation with serum. Hemolysis is quantitated spectrophotometrically by the absorbance of hemoglobin at 415 nm.

MATERIALS

EA cells: Sheep erythrocyte-antibody conjugates stored at $10^9$ cells/ml in DGVB (Veronal buffer plus $Ca^{++}$ and $Mg,^{++}$, 2.5% w/v dextrose and 0.05% w/v gelatin, 0.01% sodium azide)[1]

ER cells: Rabbit erythrocytes stored at $10^9$ in Alsevers buffer, 0.01% sodium azide.[2]

NHS: Normal human serum.

h NHS: Normal human serum incubated at 56° C. for 1 hour to inactivate complement components.

TITER SERUM FOR OPTIMUM LYSIS

A) All materials and reagents must be kept at 4° C. unless otherwise specified.

B) Wash EA cell (classical pathway) and ER cell (alternative pathway) suspensions with at least an equal volume of $PBS^{++}$ (Phosphate buffered saline, with 0.15 mM $Ca^{++}$ and 0.5 mM $Mg^{++}$). Spin at 2000 rpm for 5 minutes, decant supernatant and resuspend cells. Wash cells twice or until supernatant is obviously clear of any lysed cellular debris.

C) After the final wash, cells should be resuspended in an appropriate volume of $PBS^{++}$ so there are approximately $5\times10^8$ cells/ml. Dilute cell suspension 1:30 with distilled water and determine the absorbance at 541 nm spectrophotometrically. An adsorbance of 0.175 indicates $5\times10^8$ cells/ml. Adjust the volume of the cell suspension accordingly with $PBS^{++}$ to get a final concentration of $2.5\times10^8$ cells/ml.

D) Initially dilute the NHS and h NHS 1:40 for EA cell assay and 1:10 for ER cell assay with $PBS^{++}$.

E) Incubate at 37° C. for 1 hour:

| | |
|---|---|
| Background Control: | 100 μl h NHS<br>100 μl $PBS^{++}$<br>50 μl cells<br>($2.5 \times 10^8$ cells/ml) |

F) After 1 hour, dilute control and samples with 750 μl cold $PBS^{--}$ (Phosphate buffered saline, without $Ca^{++}$ and $Mg^{++}$) Spin for 10 minutes at 2000 rpm.

G) Read absorbance (Abs) of the supernatant at 415 nm to determine cell lysis. Include a 100% lysis tube prepared by adding 50 μl of the $2.5\times10^8$ cells/ml suspension to 950 μl distilled water.

$$\text{H) }\%\ \text{Lysis} = \frac{(\text{Abs of Sample}) - (\text{Abs of Background})}{(\text{Abs of 100\% Lysis Tube}) - (\text{Abs of Back.})}$$

I) Vary the volume of diluted serum within the 100 μl volume specified and/or adjust the initial dilution until 70-80%lysis is observed. 75% lysis is optimum for use in hemolytic assays.

J) Calculate the final serum dilution which yields 75% lysis of cells in the titer and use that dilution in the hemolytic assay.

PROCEDURE a) Use EA and ER cells from titer if prepared on same day, or prepare new cell suspension in $PBS^{++}$ daily as described in the titer procedure.

b) Dissolve inhibitors (or other agents to be tested) in $PBS^{++}$ at 500 μM. Check the pH of the solutions; adjust with minimum volume of 0.5M $Na_2HPO_4$ if pH is out of the range of 7.0 to 7.6 (pH of $PBS^{++}$ is 7.4)

c) Dilute NHS and h NHS initially so that 100 ul of that dilution in a total of 250 μl will equal the final dilution calculated in the titer assay. (Dilution will differ for EA and ER cells).

d) Incubate at 37° C. for 1 hour:

| | |
|---|---|
| Background Control: | 100 μl h NHS<br>100 μl $PBS^{++}$ |
| Normal lysis Control: | 100 μl NHS<br>100 μl $PBS^{-+}$ |
| Negative Control: | 100 μl h NHS<br>100 μl Agent being used |
| Sample: | 100 μl NHS<br>100 μl Test agent/$PBS^{++}$ |

To each tube add 50 μl of $2.5\times10^8$ cells/ml suspension:

EA cells-classical pathway,

ER cells-alternative pathway.

e. Follow steps 6 through 8 in the titer procedure.

f. Calculation of % inhibition of hemolysis (inhibition of complement activation) is as follows:

$$(1-(\%\ \text{Lysis of Sample}/\%\ \text{Normal Lysis}))\times 100$$

[1]D. M. Weir, M.D., ed. *Handbook of Experimental Immunology,* Volume 1, 2nd edition, 1973, p. 5.7. Modification to this procedure: incubate sheep erothrycytes with antibody for 30 minutes at 37° C. and on ice for 30 minutes.

[2]Collected from a rabbit ear vein directly into Alsever's buffer. Cells are spun at 2000 rpm for 5 minutes and resuspended at $1\times10^9$ cells/ml.

C1s AND FACTOR D ASSAY

Materials and Methods

Proteins and Reagents

Sodium boro[$^3$H]hydride (23.5 Ci/mmol) was obtained from Amersham Corp. as a solution in 0.1N sodium hydroxide.

Highly purified C3, C4, Factor D, Factor B, and C1s were prepared from pooled human plasma. Factors B and C4 were radiolabeled by periodate oxidation of sialic acid residues, followed by reduction with tritiated sodium borohydride. In a representative experiment, a solution of 1.2 mg of factor B in 1.8 ml of PBS was treated with 70 μl of 0.1M $NaIO_4$. After 10 min incubation on ice, excess reagent was removed by filtration over "SEPHADEX ®" which is a matrix for gel chromatography (1.0 cm×20 cm). To the protein pool was added 60 μl of $NaB[^3H]_4$ solution and incubated for 30 min on ice. Labeled protein was separated from excess reagent by desalting or dialysis. Human C4 was radiolabeled in the same manner. Radiolabeled proteins were stored at −70° C. in PBS. The specific radioactivity of $^3H$ factor B was about 10,000 CPM/μg and that of $^3H$-C4 was 5,000 CPM/μg.

C1s Assay by Inhibition of Fluid Phase C4 Activation

The cleavage of C4 was studied by incubating 10 μg of tritiated C4 with 3-5 ng of C1s at 37° C. for 30 min in 100 μl of PBS (pH 7.10) containing different concentrations of inhibitor. The reaction was stopped by the addition of 2-mercaptoethanol. The extent of cleavage was analyzed by SDS-polyacrylamide gel electrophoresis. The stained bands corresponding to C4α and C4α' were cut out and sliced. The radioactivity of the fragments was measured by liquid scintillation counting. The percent cleavage of the reaction was calculated as follows:

$$\% \text{ cleavage} = \frac{\alpha'}{\alpha + \alpha'} \times 100$$

α = radioactivity (CPM) of C4α
α' = radioactivity (CPM) of C4α'

Factor D Assay By Inhibition of Fluid Phase Factor B Activation

The effect of the peptides on Factor D-dependent cleavage of factor B was studied by incubating 3.5 μg of Factor B, 1.5 μg of $C3(H_2O)$ and 0.2 μl of Factor D at 37° C. for 60 min in Mg-PBS containing different concentrations of inhibitor. Uncleaved Factor B and its fragments, Ba and Bb, were first separated by SDS-PAGE and analyzed as described above. The percent cleavage of the reaction was calculated as follows:

$$\% \text{ cleavage} = \frac{Bb + Ba}{B + Bb + Ba} \times 100$$

B=radioactivity (CPM) of uncleaved factor B
Bb=radioactivity (CPM) of fragment Bb
Ba=radioactivity (CPM) of fragment Ba

SDS-PAGE

Electrophoresis was carried out under reducing conditions in the Laemmli system using slab gel of 8% polyacrylamide. The gels were stained and destained (Fairbanks et al. *Biochemistry* (1971) 10:2606).

Estimation of $IC_{50}$ of the Reactions

The percent inhibition of the reaction was calculated according to the following relationship:

$$\% \text{ inhibition} = \frac{A - B}{A} \times 100$$

A: % cleavage without inhibitor
B: % cleavage with inhibitor

The concentration inducing 50% inhibition was obtained by plotting the percent inhibition on a probability graph (National Blank Book Co., No. 12-083) on the ordinate and the log of the inhibitor concentration on the abscissa. From this graph, a 50% inhibition concentration $IC_{50}$ was obtained and this value was employed to express the activity.

Coagulation Inhibition Assay

Inhibitory activity of subject peptides toward thrombin and Factor Xa were done in the following manner.

Thrombin Inhibition

Mix 100 μL Thrombin (3.125 units/ml, 1.125 μg/ml) in TAB with 100 pL Peptide in TAB and incubate for 1 minute at 37° C. Add 50 μL Fibrinogen (2 mg/ml)and measure clotting end point (in seconds) in a Fibrometer (BBL)

Factor $X_a$ Inhibition

Mix 50 μL Factor $X_a$ (0.1 μg/ml) in TBSA with 100 μL Peptide in TBSA and 50 μL $CaCl_2$ 25 mM and incubate for 1 minute at 37° C. Add 50 μL Factor X deficient plasma/RBC (10/1) and measure clotting end point (in seconds) in a Fibrometer (BBL)

TAB=Thrombin Assay Buffer: 0.15M NaCl, 6.6 gm/L PEG-6000, 0.01M Imidazole, 0.01 $CaCl_2$, pH 7.4

TBSA=Tris-Saline with Bovine Serum Albumin: 0.1M NaCl,0.05 M Tris-HCl, 1 mg/ml BSA, 0.1% $NaN_3$ Factor X deficient plasma: George King Biomedical (GK 1004) RBC=Rabbit Brain Cephalin: Sigma Chemical Co. St. Louis, Mo.

Plasma Kallikrein Assay

Buffer 150 mM Tris·HCl, pH 8.0

Substrate Benzyl-Pro-Phe-Arg-pNa (Chromozym PK, Boeringer Mannheim), 10 mM in deionized water.

Enzyme Plasma Kallikrein (Sigma, K-3126), 0.0312 μ/ml. Used undiluted.

Inhibitor Dissolved at desired concentrations in deionized water or DMSO plus deionized water depending on solubility.

Assay

Control (Total Volume 1 ml)

1. 40 μl enzyme
2. 885 μl buffer
3. 25 μl DMSO
4. Incubate mixture for 5 min at 25° C.
5. Add 50 μl substrate
6. Measure rate spectrophotometrically at 405 mM at 25° C.

Inhibitor (Total Volume 1 ml)

1. 40 μl enzyme
2. Add appropriate volume of peptide solution
3. Add adjusted volume of buffer compensating for volume of peptide solution.
4. Add an adjusted volume of DMSO to maintain a final amount of 25 μl in the assay
5. Incubate mixture for 5 min at 25° C.
6. Add 50 μl substrate
7. Measure rate spectrophotometrically at 405 mM at 25° C.

Inhibition (%) is calculated in the same manner as in previous assays.

Plasmin Assay

Substrate H-D-Val-Leu-Lys-pNA·HCl (S2251, Kabi), 10 mM in deionized water; may be frozen for future use.

Buffer 50 mM Tris·HCl, pH 7.4 containing 0.01% Tween 80

Inhibitor 400 $\mu$M in deionized water

Enzyme Plasmin; 0.5 U/ml in buffer (Cat #P-4895, Sigma Chemical Co., St. Louis, Mo.)

Procedure

Mix 220 $\mu$L buffer, 200 $\mu$L deionized water (control) or inhibitor solution and 40 $\mu$L substrate. Incubate for 2 min at 37° C. Transfer 230 $\mu$L to a microcuvette, add 40 $\mu$L of enzyme, mix, and measure rate spectrophotometrically at 405 nm for about 5 min. Inhibition (%) is calculated in the same manner as in previous assays.

Tissue Plasminogen Activator (tPA) Assay

Substrate H-D-Ile-Pro-Arg-pNA·2HCl (S2288, Kabi), 10 mM in deionized water; may be frozen for future use.

Buffer 50 mM Tris·HCl, pH 7.4 containing 0.01% Tween 80.

Inhibitor 500 mM in deionized water.

Enzyme tPA, 2 chain activity standard (Catalog #116, American Diagnostica, Inc.); stock solution=10 $\mu$L of original solution per mL in buffer.

Procedure

Mix 200 $\mu$L of buffer, 200 $\mu$L of deionized water (control) or inhibitor solution and 40 $\mu$L of substrate solution. Incubate for 2 min. at 37° C., add 40 $\mu$L of enzyme, mix, and measure rate spectrophotometrically at 405 nm for about 5 min. Inhibition (%) is calculated in the same manner as in previous assays.

EXAMPLES

The following examples are included to more fully elucidate the practice of the present invention and are not intended to limiting the scope of the invention described herein. Unless otherwise noted, serine protease inhibitors cumulatively described by TABLE I (functional site recognition sequence) and TABLE II (inhibitory core sequence) were prepared by the solid-phase synthesis method described above. TABLES III,IV and V provide information on the derivation of the serine protease inhibitors listed in TABLES I and II. The peptides listed in TABLES I and II differed from the core sequences of FIGS. 1-3 by substituting leucine for methionine to facilitate synthesis and purification. This substitution is permitted by virtue of their functional identity.

TABLE I

| Peptide | Functional Site Recognition Sequence | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| | -30 | -29 | -28 | -27 | -26 | -25 | -24 | -23 | -22 | -21 | -20 | -19 | -18 | -17 | -16 | -15 | -14 | -13 | -12 | -11 | -10 | -9 | -8 | -7 | -6 | -5 | -4 | -3 | -2 | -1 | 0 |
| 1 | | | | | | | | | | | | | | | | | | | | | | | | | | | | | pro | pro | glu |
| 2 | | | | | | | | | | | | | | | | | | | | | | | | | | | pro | asn | arg | val | thr |
| 3 | | | | | | | | | | | | | | | | | | | | | | | | | | | | | | | ile |
| 4 | | | | | | | | | | | | | | | | | | | | phe | leu | glu | ala | ile | pro | met | ser | ile | pro | pro | glu |
| 5 | | | | | | | | | | | | | | | | | | | | ile | ala | gly | arg | ser | leu | asn | pro | asn | pro | pro | glu |
| 6 | | | | | | | | | | | | | | | | | | | | thr | leu | leu | ser | ala | leu | val | glu | thr | pro | pro | glu |
| 7 | | | | | | | | | | | | | | | | | | | | | ala | gly | arg | ser | leu | asn | pro | asn | arg | val | thr |
| 8 | | | | | | | | | | | | | | | | | | | | phe | leu | glu | ala | ile | pro | met | ser | ile | pro | pro | thr |
| 9 | | | | | | | | | | | | | | | | | | | | thr | leu | leu | ser | ala | leu | val | glu | thr | arg | val | thr |
| 10 | | | | | | | | | | | | | | | | | | | | thr | leu | leu | ser | ala | leu | val | glu | thr | arg | thr | ile |
| 11 | | | | | | | | | | | | | | | | | | | | | ala | gly | arg | ser | leu | asn | pro | asn | arg | thr | ile |
| 12 | | | | | | | | | | | | | | | | | | | | phe | leu | glu | ala | ile | pro | met | ser | ile | arg | thr | ile |
| 13 | | | | | | | | | | | | | | | | | | | | gly | val | arg | gly | pro | arg | val | val | glu | arg | val | thr |
| 14 | | | | | | | | | | | | | | | | | | | | | leu | gln | arg | ala | leu | glu | ile | leu | arg | val | thr |
| 15 | | | | | | | | | | | | | | | | | thr | ala | val | val | ile | ala | gly | arg | ser | leu | asn | pro | arg | arg | |
| 16 | | | | | | | | | | | | | | | | | | | | ser | pro | phe | arg | ser | val | gln | val | met | arg | val | thr |
| 17 | | | | | | | | | | | | | | | | | | | | | arg | pro | pro | gly | phe | ser | pro | phe | arg | val | thr |
| 18 | | | | | | | | | | | | | | | | | | | | ile | asp | gly | arg | ile | val | glu | gly | ser | arg | val | thr |
| 19 | | | | | | | | | | | | | | | | | | | | phe | leu | glu | ala | ile | pro | met | ser | ile | pro | pro | ile |
| 20 | | | | | | | | | | | | | | | | | | | | | | | | | | | | | | | |
| 21 | | | | | | | | | | | | | | | | | | | | | | | | | | | | | arg | val | thr |
| 22 | | | | | | | | | | | | | | | | | | | | | | | | | | | | | | | ile |
| 23 | | | | | | | | | | | | | | | | | | | | | | | | | | | | | | | |
| 24 | | | | | | | | | | | | | | | | | | | | phe | leu | glu | ala | ile | pro | met | ser | ile | pro | pro | glu |
| 25 | | | | | | | | | | | | | | | | | | | | ile | ala | gly | arg | ser | leu | asn | pro | asn | arg | val | thr |
| 26 | | | | | | | | | | | | | | | | | | | | thr | leu | leu | ser | ala | leu | val | glu | thr | arg | thr | ile |
| 27 | | | | | | | | | | | | | | | | | | | | | ala | gly | arg | ser | leu | asn | pro | asn | arg | val | thr |
| 28 | | | | | | | | | | | | | | | | | | phe | leu | glu | ala | ile | pro | met | ser | ile | pro | pro | arg | val | thr |
| 29 | | | | | | | | | | | | | | | | | | | | thr | leu | leu | ser | ala | leu | val | glu | thr | arg | val | thr |
| 30 | | | | | | | | | | | | | | | | | | | | thr | leu | leu | ser | ala | leu | val | glu | thr | arg | thr | ile |
| 31 | | | | | | | | | | | | | | | | | | | | | | ile | ala | gly | arg | ser | leu | asn | pro | asn | ile |
| 32 | | | | | | | | | | | | | | | | | | | | phe | leu | glu | ala | ile | pro | met | ser | ile | pro | pro | ile |
| 33 | | | | | | | | | | | | | | | | | | | | ile | ala | gly | arg | ser | leu | asn | pro | asn | arg | val | thr |
| 34 | | | | | | | | | | | | | | | | | | | | gly | val | arg | gly | pro | arg | val | val | glu | arg | val | thr |
| 35 | | | | | | | | | | | | | | | | | | | | | leu | gln | arg | ala | leu | glu | ile | leu | arg | val | thr |
| 36 | | | | | | | | | | | | | | | | | | | | glu | ala | gly | val | asp | ala | ala | ser | val | ser | glu | glu |
| 37 | | | | | | | | | | | | | | | | | | | | | | | | | | | | | | | |
| 38 | | | | | | | | | | | | | | | | | | | | | | | | | | | | | | | |
| 39 | | | | | | | | | | | | | | | | | | | | | | | | | | | | | | | |
| 40 | | | | | | | | | | | | | | | | | | | | | | | | | | | | | | | |
| 41 | | | | | | | | | | | | | | | | | | | | | | | | | | | | | | | |
| 42 | | | | | | | | | | | | | | | | | | | | | | | | | | | | | | | |
| 43 | | | | | | | | | | | | | | | | | | | | | | | | | | | | | | | |
| 44 | | | | | | | | | | | | | | | | | | | | | | | | | | | | | | | |
| 45 | | | | | | | | | | | | | | | | | | | | ile | ala | gly | arg | ser | leu | asn | pro | asn | arg | val | thr |
| 46 | | | | | | | | | | | | | | | | | | | | | | | | | | | | | | | |
| 47 | | | | | | | | | | | | | | | | | | lys | ala | pro | gly | arg | val | val | gly | gly | ala | val | arg | val | thr |
| 48 | | | | | | | | | | | | | | | | | | | | | | | | | | | | | | | glu |
| 49 | | | | | | | | | | | | | | | | | | | | | ala | val | ile | val | ser | ala | arg | met | ala | pro | glu |
| 50 | | | | | | | | | | | | | | | | | | val | ala | arg | thr | leu | leu | val | phe | glu | val | gln | arg | val | thr |

TABLE I-continued

| Peptide | Functional Site Recognition Sequence | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| | -30 | -29 | -28 | -27 | -26 | -25 | -24 | -23 | -22 | -21 | -20 | -19 | -18 | -17 | -16 | -15 | -14 | -13 | -12 | -11 | -10 | -9 | -8 | -7 | -6 | -5 | -4 | -3 | -2 | -1 | 0 |
| 51 | | | | | | | | | | | | | | | | | | | | | | | | | | | | | | | |
| 52 | | | | | | | | | | | | | | | | | | | | | | ser | met | pro | leu | lys | val | asp | leu | val | asp |
| 53 | | | | | | | | | | | | | | | | | | | | | | | | | | | | | arg | val | thr |
| 54 | arg | asp | lys | gly | gln | ala | gly | leu | gln | arg | glu | leu | glu | ile | leu | gln | glu | glu | asp | leu | ile | asp | glu | asp | asp | ile | pro | val | arg | val | thr |
| 55 | arg | asp | lys | gly | gln | ala | gly | leu | gln | arg | ala | leu | glu | ile | leu | gln | glu | glu | asp | leu | ile | asp | glu | asp | | | | | arg | val | thr |
| 56 | arg | asp | lys | gly | gln | ala | gly | leu | gln | arg | ala | leu | | | | | | | | | | | | | | | | | arg | val | thr |
| 57 | arg | asp | lys | gly | gln | ala | gly | leu | gln | arg | ala | leu | glu | ile | leu | gln | | | | | | | | | | | | | arg | val | thr |
| 58 | arg | asp | lys | gly | gln | ala | gly | leu | gln | arg | ala | leu | glu | ile | leu | gln | glu | glu | asp | leu | | | | | | | | | arg | val | thr |

TABLE II

| Inhibitory Sequence | | | | | | | | | | | | | | | | | |
|---|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | 17 | Peptide |
| val | lys | phe | asn | lys | pro | phe | val | phe | leu | ile | | | | | | | 1 |
| phe | lys | ala | asn | arg | pro | phe | leu | val | phe | ile | | | | | | | 2 |
| val | arg | phe | asn | arg | pro | phe | leu | leu | ile | ile | | | | | | | 3 |
| val | lys | phe | asn | lys | pro | phe | val | phe | leu | ile | | | | | | | 4 |
| val | lys | phe | lys | asn | pro | phe | val | phe | leu | ile | | | | | | | 5 |
| val | lys | phe | lys | asn | pro | phe | val | phe | leu | ile | | | | | | | 6 |
| phe | lys | ala | asn | arg | pro | phe | leu | val | phe | ile | | | | | | | 7 |
| phe | lys | ala | asn | arg | pro | phe | leu | val | phe | ile | | | | | | | 8 |
| phe | lys | ala | asn | arg | pro | phe | leu | val | phe | ile | | | | | | | 9 |
| val | arg | phe | asn | arg | pro | phe | leu | leu | ile | ile | | | | | | | 10 |
| val | arg | phe | asn | arg | pro | phe | leu | leu | ile | ile | | | | | | | 11 |
| val | arg | phe | asn | arg | pro | phe | leu | leu | ile | ile | | | | | | | 12 |
| phe | lys | ala | asn | arg | pro | phe | leu | val | phe | ile | | | | | | | 13 |
| phe | lys | ala | asn | arg | pro | phe | leu | val | phe | ile | | | | | | | 14 |
| | | | | | | | | | | | | | | | | | 15 |
| phe | lys | ala | asn | arg | pro | phe | leu | val | phe | ile | | | | | | | 16 |
| phe | lys | ala | asn | arg | pro | phe | leu | val | phe | ile | | | | | | | 17 |
| phe | lys | ala | asn | arg | pro | phe | leu | val | phe | ile | | | | | | | 18 |
| val | arg | phe | asn | arg | pro | phe | leu | leu | ile | ile | | | | | | | 19 |
| val | lys | phe | asn | lys | pro | phe | val | phe | leu | leu | ile | glu | gln | asn | thr | lys | 20 |
| phe | lys | ala | asn | arg | pro | phe | leu | val | phe | ile | arg | glu | val | pro | leu | asn | 21 |
| val | arg | phe | asn | arg | pro | phe | leu | leu | ile | ile | val | pro | thr | asp | thr | gln | 22 |
| leu | arg | tyr | asn | lys | pro | phe | ile | leu | val | leu | phe | glu | thr | pro | gly | asn | 23 |
| val | lys | phe | asn | lys | pro | phe | val | phe | leu | leu | ile | glu | gln | asn | thr | lys | 24 |
| val | lys | phe | asn | lys | pro | phe | val | phe | leu | leu | ile | glu | gln | asn | thr | lys | 25 |
| val | lys | phe | asn | lys | pro | phe | val | phe | leu | leu | ile | glu | gln | asn | thr | lys | 26 |
| phe | lys | ala | asn | arg | pro | phe | leu | val | phe | ile | arg | glu | val | pro | leu | asn | 27 |
| phe | lys | ala | asn | arg | pro | phe | leu | val | phe | ile | arg | glu | val | pro | leu | asn | 28 |
| phe | lys | ala | asn | arg | pro | phe | leu | val | phe | ile | arg | glu | val | pro | leu | asn | 29 |
| val | arg | phe | asn | arg | pro | phe | leu | leu | ile | ile | val | pro | thr | asp | thr | gln | 30 |
| val | arg | phe | asn | arg | pro | phe | leu | leu | ile | ile | val | pro | thr | asp | thr | gln | 31 |
| val | arg | phe | asn | arg | pro | phe | leu | leu | ile | ile | val | pro | thr | asp | thr | gln | 32 |
| leu | arg | tyr | asn | lys | pro | phe | ile | leu | val | leu | phe | glu | thr | pro | gly | asn | 33 |
| phe | lys | ala | asn | arg | pro | phe | leu | val | phe | ile | arg | glu | val | pro | leu | asn | 34 |
| phe | lys | ala | asn | arg | pro | phe | leu | val | phe | ile | arg | glu | val | pro | leu | asn | 35 |
| phe | arg | ala | asp | his | pro | phe | leu | phe | cys | ile | lys | his | ile | ala | thr | asn | 36 |
| | | | | arg | pro | phe | leu | val | phe | ile | arg | glu | val | pro | leu | asn | 37 |
| | | | | arg | pro | phe | leu | val | phe | ile | | | leu | pro | gly | | 38 |
| | | | | arg | pro | phe | leu | val | phe | ile | | | leu | pro | asn | | 39 |
| | | | | arg | pro | phe | leu | val | phe | ile | arg | | pro | gly | asp | | 40 |
| | | | | arg | pro | phe | leu | val | phe | ile | arg | | pro | asn | asp | | 41 |
| | | | | arg | pro | phe | leu | val | phe | ile | | | leu | pro | asn | | 42 |
| | | | | | pro | phe | leu | val | phe | ile | | | leu | pro | asn | | 43 |
| | | | | arg | pro | phe | leu | val | phe | ile | | | leu | pro | asn | | 44 |
| phe | lys | ala | asn | arg | pro | phe | cys | val | phe | ile | arg | glu | val | pro | leu | asn | 45 |
| | | | | arg | pro | phe | leu | val | phe | | | | leu | pro | asn | | 46 |
| val | lys | phe | asn | lys | pro | phe | val | phe | leu | leu | ile | glu | gln | asn | thr | lys | 47 |
| ile | ile | leu | pro | arg | pro | phe | leu | phe | val | val | arg | his | asn | pro | thr | ser | 48 |
| ile | ile | leu | pro | arg | pro | phe | leu | phe | val | val | arg | his | asn | pro | thr | ser | 49 |
| phe | lys | ala | asn | arg | pro | phe | leu | val | phe | ile | arg | glu | val | pro | leu | asn | 50 |
| phe | val | ala | asn | his | pro | phe | leu | phe | leu | ile | arg | glu | asp | ile | ala | gly | 51 |
| phe | val | ala | asn | his | pro | phe | leu | phe | leu | ile | arg | glu | asp | ile | ala | gly | 52 |
| phe | lys | ala | asn | arg | pro | phe | leu | val | phe | ile | arg | glu | val | pro | leu | asn | 53 |
| phe | lys | ala | asn | arg | pro | phe | leu | val | phe | ile | | | | | | | 54 |
| phe | lys | ala | asn | arg | pro | phe | leu | val | phe | ile | | | | | | | 55 |
| phe | lys | ala | asn | arg | pro | phe | leu | val | phe | ile | | | | | | | 56 |
| phe | lys | ala | asn | arg | pro | phe | leu | val | phe | ile | | | | | | | 57 |
| phe | lys | ala | asn | arg | pro | phe | leu | val | phe | ile | | | | | | | 58 |

| 18 | 19 | 20 | 21 | 22 | 23 | 24 | 25 | 26 | 27 | 28 | 29 | 30 | 31 | 32 | Peptide |
|---|---|---|---|---|---|---|---|---|---|---|---|---|---|---|---|
| | | | | | | | | | | | | | | | 1 |
| | | | | | | | | | | | | | | | 2 |
| | | | | | | | | | | | | | | | 3 |
| | | | | | | | | | | | | | | | 4 |
| | | | | | | | | | | | | | | | 5 |
| | | | | | | | | | | | | | | | 6 |
| | | | | | | | | | | | | | | | 7 |
| | | | | | | | | | | | | | | | 8 |
| | | | | | | | | | | | | | | | 9 |
| | | | | | | | | | | | | | | | 10 |
| | | | | | | | | | | | | | | | 11 |
| | | | | | | | | | | | | | | | 12 |
| | | | | | | | | | | | | | | | 13 |
| | | | | | | | | | | | | | | | 14 |
| | | | | | | | | | | | | | | | 15 |
| | | | | | | | | | | | | | | | 16 |
| | | | | | | | | | | | | | | | 17 |
| | | | | | | | | | | | | | | | 18 |
| | | | | | | | | | | | | | | | 19 |

TABLE II-continued

| Inhibitory Sequence | | | | | | | | | | | | | | | |
|---|---|---|---|---|---|---|---|---|---|---|---|---|---|---|---|
| ser | pro | leu | phe | leu | gly | lys | val | val | asn | pro | thr | gln | lys | | 20 |
| thr | ile | ile | phe | leu | gly | arg | val | ala | asn | pro | | | | | 21 |
| asn | ile | phe | phe | leu | ser | lys | val | thr | asn | pro | ser | lys | pro | arg | 22 |
| ser | leu | val | phe | leu | gly | arg | ile | ser | asn | pro | ala | thr | lys | | 23 |
| ser | pro | leu | phe | leu | gly | lys | val | val | asn | pro | thr | gln | lys | | 24 |
| ser | pro | leu | phe | leu | gly | lys | val | val | asn | pro | thr | gln | lys | | 25 |
| ser | pro | leu | phe | leu | gly | lys | val | val | asn | pro | thr | gln | lys | | 26 |
| thr | ile | ile | phe | leu | gly | arg | val | ala | asn | pro | | | | | 27 |
| thr | ile | ile | phe | leu | gly | arg | val | ala | asn | pro | | | | | 28 |
| thr | ile | ile | phe | leu | ser | lys | val | ala | asn | pro | | | | | 29 |
| asn | ile | phe | phe | leu | ser | lys | val | thr | asn | pro | ser | lys | pro | arg | 30 |
| asn | ile | phe | phe | leu | ser | lys | val | thr | asn | pro | ser | lys | pro | arg | 31 |
| asn | ile | phe | phe | leu | ser | lys | val | thr | asn | pro | ser | lys | pro | arg | 32 |
| ser | leu | val | phe | leu | gly | arg | ile | ser | asn | pro | ala | thr | lys | | 33 |
| thr | ile | ile | phe | leu | gly | arg | val | ala | asn | pro | | | | | 34 |
| thr | ile | ile | phe | leu | gly | arg | val | ala | asn | pro | | | | | 35 |
| ala | val | leu | phe | phe | gly | arg | cys | val | ser | pro | | | | | 36 |
| thr | ile | ile | phe | leu | gly | arg | val | ala | asn | pro | | | | | 37 |
| | | ile | phe | leu | gly | arg | val | ala | asn | pro | | | | | 38 |
| | | ile | phe | leu | gly | arg | val | ala | asn | pro | | | | | 39 |
| | | ile | phe | leu | gly | arg | val | ala | asn | pro | | | | | 40 |
| | | | phe | leu | gly | arg | val | ala | asn | pro | | | | | 41 |
| | | ile | phe | leu | gly | arg | val | ala | asn | | | | | | 42 |
| | | ile | phe | leu | gly | arg | val | ala | asn | | | | | | 43 |
| | | ile | phe | leu | | arg | val | ala | asn | pro | | | | | 44 |
| thr | ile | ile | phe | leu | gly | cys | val | ala | asn | pro | ala | val | lys | | 45 |
| | | ile | | leu | | arg | val | ala | asn | pro | | | | | 46 |
| ser | pro | leu | phe | leu | gly | lys | val | val | asn | pro | thr | gly | lys | | 47 |
| thr | val | leu | phe | leu | gly | gln | val | leu | glu | pro | | | | | 48 |
| thr | val | leu | phe | leu | gly | gln | val | leu | glu | pro | | | | | 49 |
| thr | ile | ile | phe | leu | gly | arg | val | ala | asn | pro | | | | | 50 |
| val | val | val | phe | val | gly | his | val | thr | asn | pro | | | | | 51 |
| val | val | val | phe | val | gly | his | val | thr | asn | pro | ala | val | lys | | 52 |
| thr | ile | ile | phe | leu | gly | arg | val | ala | asn | pro | ala | val | lys | | 53 |
| | | | | | | | | | | | | | | | 54 |
| | | | | | | | | | | | | | | | 55 |
| | | | | | | | | | | | | | | | 56 |
| | | | | | | | | | | | | | | | 57 |
| | | | | | | | | | | | | | | | 58 |

TABLE III

| Peptide | Description |
|---|---|
| 1 | AT:361-374 |
| 2 | AT III:388-403 |
| 3 | ACT:367-378 |
| 4 | AT:352-374 |
| 5 | AT III:381-389/AT:361-374, des Asn367, Lys368; Lys367, Asn368 |
| 6 | ACT:356-364/AT:361-374, des Asn367, Lys368; Lys367, Asn368 |
| 7 | AT III:382-403 |
| 8 | AT:352-362/AT III 392-403 |
| 9 | ACT:356-364/AT III 390-403 |
| 10 | ACT:356-378 |
| 11 | AT III:382-389/ACT:365-378 |
| 12 | AT:352-360/ACT:365-378 |
| 13 | α-Fibrinogen:14-20/AT III 390-403 |
| 14 | Complement C4:75-82/AT III 390-403 |
| 15 | AT III:377-390 |
| 16 | LMW Kininogen:385-393/AT III 390-403 |
| 17 | LMW Kinin:380-387/AT III:390-403 |
| 18 | Prothrombin:319-327/AT III:390-403 |
| 19 | AT:352-362/ACT 367-378 |

TABLE IV

| Peptide | Description |
|---|---|
| 20 | AT:364-394 |
| 21 | AT III:390-420 |
| 22 | ACT:367-399 |
| 23 | GENERIC |
| 24 | AT:352-394 |
| 25 | AT III:381-392/AT:364-394 |
| 26 | ACT:356-367/AT:364-394 |
| 27 | AT III:382-420 |

TABLE IV-continued

| Peptide | Description |
|---|---|
| 28 | AT:352-362/AT III:390-420 |
| 29 | ACT:356-364/AT III:390-420 |
| 30 | ACT:356-399 |
| 31 | AT III:381-389/ACT:367-399 |
| 32 | AT:352-362/ACT:367-399 |
| 33 | AT III:381-392/GENERIC |
| 34 | α-Fibrinigen:14-22/AT III:390-420 |
| 35 | Complement C4:75-82/AT III:390-420 |
| 36 | Ovalbumin: 346-385 |
| 37 | AT III:397-420 |
| 38 | AT III:397-420 with Leu—Pro—Gly substituted for amino acids 404-411 |
| 39 | AT III:397-420 with Leu—Pro—Asn substituted for 404-411 |
| 40 | AT III:397-420 with Arg—Pro—Gly—Asp substituted for 404-411 |

TABLE V

| Peptide | Description |
|---|---|
| 41 | AT III:397-420 with Arg—Pro—Asn—Asp substituted for 404-412 |
| 42 | AT III:397-419 with Leu—Pro—Asn substituted for 404-411 |
| 43 | AT III:398-419 with Leu—Pro—Asn substituted for 404-411 |
| 44 | AT III:397-420 with Leu—Pro—Asn substituted for 404-411, des Gly415 |
| 45 | AT III:381-423, des Leu400, Gly416; Cys400, Cys416 |
| 46 | AT III:397-420 with Leu—Pro—Asn substituted for 404-411, des Ile403, Phe413, Gly415 |
| 47 | Plasminogen:556-565/AT III:390-420, des Cys557, Cys565; |

TABLE V-continued

| Peptide | Description |
|---|---|
| | Ala557, Ala565 |
| 48 | tPA inh:423–450, des Met426, Met445, Met449; Leu426, Leu445, Leu449 |
| 49 | tPA inh:412–451 des Met426, Met445, Met449; Leu426, Leu445, Leu449 |
| 50 | C1 inh:442–453/AT III:390–420 |
| 51 | Barley Protein Z:384–411 |
| 52 | Barley Protein Z:373–411 |
| 53 | AT III:390–423 |
| 54 | Complement C4:68–98/AT III:390–403 |
| 55 | Complement C4:68–91/AT III:390–403 |
| 56 | Complement C4:68–79/AT III:390–403 |
| 57 | Complement C4:68–83/AT III:390–403 |
| 58 | Complement C4:68–87/AT III:390–403 |

EXAMPLE 1

Inhibitory core sequences corresponding to peptides 20,21,22, 23, 48 and 51 were synthesized and assayed for inhibitory activity toward numerous serine proteases following the assays described above. The results of these assays are listed in the following table.

TABLE VI

| | Peptides | | | | | | | | | | | |
|---|---|---|---|---|---|---|---|---|---|---|---|---|
| | 20 | | 21 | | 22 | | 23 | | 48 | | 51 | |
| Assay | μM | %[1] | μM | % | μM | % | μM | % | μM | % | μM | % |
| Complement | | | | | | | | | | | | |
| Classical Pathway | 100 | 90 | 200 | 90 | 100 | 100 | 25 | 100 | 100 | 1 | 25 | 0 |
| C1s | 12 | 50 | 6 | 50 | 6 | 50 | NT[2] | | NT | | NT | |
| Alternative Pathway | 100 | 80 | 200 | 85 | 100 | 86 | 25 | 100 | 100 | 21 | 25 | 0 |
| Factor D | 16 | 50 | <8 | 50 | 4 | 50 | NT | | NT | | NT | |
| Coagulation | | | | | | | | | | | | |
| Factor Xa | 40 | 87 | 40 | 99 | 40 | 97 | NT | | NT | | NT | |
| Thrombin | 40 | 71 | 40 | 97 | 40 | 90 | NT | | NT | | NT | |
| Kallikrein | 50 | 0 | 100 | 55 | 50 | 58 | NT | | NT | | NT | |
| Cathepsin G | 100 | 0 | 100 | 38 | 100 | 46 | 100 | 0 | NT | | NT | |
| Plasmin | 200 | 43 | 200 | 53 | 200 | 56 | 200 | 67 | NT | | NT | |

[1]% inhibition at listed concentration
[2]not tested

It is clear from the data in Table VI that the inhibitory core sequences represented by structure I exhibit broad inhibitory activity. While not all species in the genes of Structure I perform equally, the data in the above table does show the inhibitory activity of the peptides of structure I toward serine proteases. Indeed, while peptides 20, 21 and 22, 48 and 51 are based on AT, AT III, ACT, tPA inhibitor and Barley Protein Z respectively, peptide 23 was prepared to minimize the actual sequence identity found in the former five peptides while maintaining the chemical homology described for structure I.

EXAMPLE 2

Residues 12–19 of structures (I) and (II) may be substituted for virtually any other amino acid or residues from this region may be removed altogether. The following peptides were prepared to demonstrate that residues from region $R_{12-19}$ may be removed while still maintaining inhibitor activity. Peptide 37 was prepared by deleting 7 amino acid residues from the N-terminus of Peptide 21 (AT III:390–420). Peptide 38 is similar to peptide 37, but $R_{12-19}$ were replaced with Leu-Pro-Gly. Peptide 39 is similar to peptide 37, but $R_{12-19}$ were replaced with Leu-Pro-Asn. Peptide 40 is similar to peptide 37, but $R_{13-19}$ were replaced with Pro-Gly-Asp. Peptide 41 is similar to peptide 37, but $R_{13-20}$ were replaced with Pro-Asn-Asp. Peptide 42 is similar to peptide 37, but $R_{12-19}$ were replaced with Leu-Pro-Asn and $R_{28}$ was deleted. Peptide 43 is similar to peptide 37, but $R_{12-19}$ were replaced with Leu-Pro-Asn, $R_{28}$ was deleted and $R_5$ was deleted. Peptide 44 is similar to peptide 37, but $R_{12-19}$ were replaced with Leu-Pro-Asn and $R_{23}$ was deleted. Peptide 46 is similar to peptide 37, but $R_{11-19}$ were replaced with Leu-Pro-Asn and $R_{21,23}$ were deleted. Peptide 45 is similar to peptide 53, but contains Cys residues at $R_8$ and $R_{24}$. Following the synthesis the blocking groups were removed from the Cys residues and the peptide was allowed to oxidize. Assay with Ellman's reagent indicated the absence of free sulfhydral groups. The peptide therefore was folded and contained a disulfide bridge between the two Cys residues. Peptides 47–49 are described in TABLE V.

The $R_{12-19}$ region of these peptides vary considerably in their hydrophilicity/hydrophobicity. In peptide 38 the region is substantially hydrophobic. In peptide 39 the region is considered neither hydrophobic nor hydrophilic since it contains two hydrophilic residues and two hydrophobic residues. In peptide 40 the region is substantially hydrophilic.

The inhibitory activity of Peptides 21, and 37–49 toward tissue plasminogen activator (tPA) was determined by the assay described above and the results reported in TABLE VII below. Deletion of the N-terminal residues from peptide 21 decreased inhibition only from 70% to 50% clearly indicating that this region of Structures I and II, although preferred, is not critical.

TABLE VII

| Inhibition of tPA (S2288) | |
|---|---|
| Peptide | Inhibition |
| 38 | 59[10] |
| 39 | 55[10] |
| 40 | 39[10] |
| 41 | 8[10] |
| 42 | 44[10] |
| 43 | 7[10] |
| 44 | 55[10] |
| 45 | 69[20] |
| 46 | 0[10] |
| 47 | NT |
| 48 | 0[200] |

TABLE VII-continued

| Inhibition of tPA (S2288) | |
|---|---|
| Peptide | Inhibition |
| 49 | 0[50] |

[1] bracketed value indicates μM concentration at which inhibition was determined.

Peptides 38-45 have inhibitory activity toward tPA indicating that the highly variable residues in $R_{12-19}$ are not essential for binding of peptides 38-45 to tPA. These data demonstrate that region $R_{12-19}$ of structures I and II can be either hydrophobic, hydrophilic or even shortened and not significantly affect activity. It should be understood, however, that the peptide inhibitors of the present invention may be more efficacious toward other proteases if the $R_{12-19}$ region is intact or possibly if it contains a number of amino acid residues different from those described above.

Region $R_{12-19}$ is quite variable and is a turn in the crystalline form of AT (cleared and dissociated). This coupled with the folding demonstrated in peptide 45 indicates that peptides homologous to the C-termini of serine protease inhibitors may exhibit a turn in this region. Peptides 38-40 contain residues that are frequently found in turns. While not fully understood, region $R_{12-19}$ is preferably adapted to provide a turn.

Peptides 48 and 49 which are based on the C-terminal region of the natural inhibitor of t-PA did not exhibit activity in this assay. While not fully understood, the sequence of these peptides has not been verified by sequence analysis and may be in error.

EXAMPLE 3

Inhibitory core sequences corresponding to peptides 1, 2 and 3 were synthesized and assayed for inhibitory activity toward numerous serine proteases following the assays described above.

TABLE VIII

| Assay | Peptide 1 μM | Peptide 1 %[1] | Peptide 2 μM | Peptide 2 % | Peptide 3 μM | Peptide 3 % |
|---|---|---|---|---|---|---|
| Complement | | | | | | |
| Classical Pathway | 200 | 0 | 200 | 100 | 200 | 100 |
| C1s | 200 | 0 | 34 | 50 | 55 | 50 |
| Alternative Pathway | 200 | 0 | 200 | 59 | 200 | 38 |
| Factor D | 200 | 0 | 53 | 50 | 111 | 50 |
| Coagulation | | | | | | |
| Factor Xa | 40 | 31 | 40 | 51 | 40 | 73 |
| Thrombin | 40 | 0 | 40 | 50 | 40 | 50 |
| Kallikrein | NT[2] | | 100 | 21 | NT | |
| Cathepsin G | 100 | 0 | 100 | 13 | 100 | 32 |
| Plasmin | 200 | 37 | 200 | 33 | 200 | 33 |

[1] % inhibition at stated concentration
[2] not tested

It is clear from the data in TABLE VIII that the inhibitory core sequences represented by structures III and IV exhibit broad inhibitory activity. In the genus of peptides described by either structure III or IV, it is reasonable and indeed expected that all species would not perform equally in all assays.

EXAMPLE 4

The peptide inhibitors of the present invention preferably contain a suitable functional site recognition sequence which serves to confer enhanced selectivity and in some cases increased potency.

As noted previously in the specification, elastase is the target substrate for AT; thrombin is the target substrate for AT III; and ACT is believed to act as an inhibitor of cathepsin G.

The data of TABLE IX demonstrates that useful functional site recognition sequences may be obtained from the cleavage sites of the naturally occurring protease inhibitors. For example, while the short inhibitor peptide based on AT (peptide 1) exhibits no inhibitory activity toward elastase at 200 μM; peptide 4, which consists of peptide 1 and a recognition sequence based on the cleavage site of AT, exhibits 70% inhibition toward elastase at 200 μM. Peptide 3 (shortened inhibitory core sequence based on ACT) exhibits 50% inhibition toward thrombin. Peptide 11 (Peptide 3 plus AT III cleavage site) exhibits 81% inhibition toward thrombin at the same concentration.

TABLE IX

| Peptide | 200 μM Elastase Inhibition | 40 μM Thrombin Inhibition | 200 μM Cathepsin G Inhibition |
|---|---|---|---|
| 1 | 0 | 0 | 0 |
| 4 | 70 | NT[1] | 14 |
| 5 | 0 | NT | 0 |
| 6 | 17 | NT | 0 |
| 2 | 0 | 0 | 13 |
| 7 | NT | 50 | 28 |
| 8 | 77 | 30 | 44 |
| 9 | NT | 32 | 41 |
| 3 | 0 | 50 | 32 |
| 10 | 0 | NT | 65 |
| 11 | 15 | 81 | 40 |
| 12 | 0 | NT | 51 |
| 19 | 100 | NT | NT |
| 20 | 0 | 71 | 0 |
| 24 | 26 | NT | 0 |
| 25 | 0 | NT | 35 |
| 26 | NT | NT | 0 |
| 21 | 0 | 97 | 38 |
| 27 | 0 | 97 | 52 |
| 28 | 0 | NT | 16 |
| 29 | NT | NT | 0 |
| 22 | 0 | 90 | 46 |
| 30 | NT | NT | 38 |
| 31 | 0 | NT | 54 |
| 32 | 0 | NT | 0 |
| 23 | 0 | NT | 0 |
| 33 | 0 | NT | 35 |

[1] Not tested

Although the data show some cross reactivity, the data also show that the functional site recognition sequence from the naturally occurring protease inhibitor confers selectivity for the subject protease to the particular inhibitory core sequence and in some cases also increases potency. Thus, inhibition can be enhanced by varying the site of fusion to the inhibitory core as discussed above and can be further enhanced by extending the functional site recognition site in the N-terminal direction.

EXAMPLE 5

Numerous peptides were synthesized based on the short and long inhibitory core sequences represented by peptides 2 and 21. Functional site recognition sequences were fused to the above inhibitory core peptides and the resulting peptides assayed for inhibitory activity toward complement activation. The following table lists the data for the inhibition of complement activation: classical pathway (CP); alternative pathway (AP); Factor D (D) and protease C1s (C1s).

TABLE X

| Peptide | % inhibition CP | AP | IC50[3] D | C1S |
|---|---|---|---|---|
| 2 | 100[200] | 59[200] | 53 | 34 |
| 21 | 100[200][1] | 86[50] | <8 | 6 |
| 7 | 100[50] | 100[50] | 145 | 39 |
| 27 | 86[5] | 65[5] | <25 | 12 |
| 13 | 75[25] | 61[25] | <50 | 33 |
| 34 | 100[5] | 45[5] | NT[2] | NT |
| 14 | 40[25] | 0[25] | 8 | 9 |
| 35 | 100[50] | 87[100] | NT | NT |
| 16 | 100[50] | 58[100] | NT | NT |
| 17 | 98[100] | 53[100] | NT | NT |
| 18 | 100[50] | 20[50] | 43 | 40 |
| 32 | 90[200] | 0[200] | NT | NT |
| 36 | 25[200] | 0[200] | NT | NT |
| 47 | 88[25] | 34[25] | NT | NT |
| 48 | 0[100] | 21[100] | NT | NT |
| 49 | 17[100] | 35[100] | NT | NT |
| 50 | 97[25] | NT | NT | NT |
| 52 | 19[50] | 16[50] | NT | NT |
| 53 | 100[6] | 100[6] | NT | NT |

[1]bracket value indicates μM concentration at which inhibition was determined
[2]not tested
[3]indicates μM concentration at which protease was inhibited 50%

The above data demonstrates that useful functional site recognition sequences are not limited to those which are derived from or homologous to the cleavage site region of the naturally-occurring inhibitor. Indeed it is clear that one can synthesize functional site recognition sequences which do not resemble the natural cleavage sites and that these recognition sequences may perform better than the naturally occurring ones. Such variations are easily accomplished following the teachings herein.

EXAMPLE 6

These exemplary peptide inhibitors (peptides 13, 7 and 27) were assayed for in vivo activity in inhibiting complement activation using the reverse passive arthus reaction (RPAR). RPAR is a model of complement-mediated damage due to activation via interaction with antigen/antibody complexes. Female guinea pigs (400 gm) were pretreated intracardially with bovine serum albumin and Evans blue dye. Ninety minutes later they received bilateral intradermal injections of peptide inhibitor or control material in the thoracolumbar region. Injection sites were excised postmortem and fixed in 10% buffered formalin for pathological evaluation. The peptides were administered to obtain an initial level of 25 mM in the circulatory system.

The histopathological results are outlined below. The degree of inflammation was scored as follows: 0 indicating no acute inflamation; 1 indication minimal acute inflammation; 2 indicating mild acute inflammation; and 3 indicating moderate acute inflammation.

a) Antibody Only (Anti-Bovine Serum Albumin)

Acute Inflammation (mean score; 3) characterized by an intramural and perivascular neutrophilic infiltrate in the postcapillary vessels.

b) Protease Inhibitors Only

1) Peptide 13; no tissue changes-mean score; 0
2) Peptide 7; no tissue changes-mean score; 0
3) Peptide 27; mild acute inflammation centered around postcapillary vessels-mean score; 1 c) Antibody plus Protease Inhibitors

1) Peptide 13+Antibody—mean score; 1
2) Peptide 7+Antibody—mean score; 2
3) Peptide 27+Antibody—mean score; 3

INTERPRETATION

Animals receiving anti-bovine serum albumin intradermally developed an acute inflammation at the injection site which was centered around post-capillary vessels.

Those animals receiving protease inhibitors intradermally did not show significant inflammation at the injection site except for animals receiving peptide 27 which developed a mild neutrophilic perivascular infiltrate.

Animals receiving antibody plus protease inhibitors generally had a less intense acute inflammation than those receiving antibody only. The exception was peptide 27. The possibility exists that the inflammation exhibited by Peptide 27 alone obscured the ability of this compound to prevent inflammation when tested with anti-bovine serum albumin.

EXAMPLE 7

Variations of peptide 14 (C4: 75–82/AT III: 390–403) were prepared which represent different fusions of a functional site recognition sequence from complement C4 and the short inhibitory core sequence of AT III. Complement inhibition data for peptides 54, 55, 56, 57 and 58 are compared to that previously reported for peptide 14 (Example 5) in the table below.

TABLE XI

| Peptide | % Inhibition CP | AP |
|---|---|---|
| 14 | 40[25][1] | 0[25] |
| 54 | 0[50] | 0[50] |
| 55 | 0[100] | 0[100] |
| 56 | 39[100] | 0[100] |
| 57 | 82[50] | 100[50] |
| 58 | 0[50] | 0[50] |

[1]bracketed value indicates μM concentration at which inhibition was determined.

These data show the importance of the fusion site between the functional site recognition sequence and the inhibitory core sequence as described above. Expanding the distance between the cleavage site of the native substrate (e.g. C4) from the inhibitory core sequence impacts the inhibitory activity of the peptide (e.g. peptides 54, 56 and 58). Peptides having similar fusion points (e.g. peptides 56 and exhibited similar activity.

We claim:

1. A serine protease inhibitor peptide consisting of the structure:

$$R_{1-5}\text{-Pro-}R_{7-11}\text{-}R_{12-19}\text{-}R_{20-27}\text{-Pro-}R_{29-31}$$

in which R is a naturally occurring amino acid residue or synthetic analog thereof; $R_{1-5}$ is a substantially hydrophilic region, $R_{7-11}$ is a substantially hydrophobic region, $R_{12-19}$ represents a region containing hydrophobic residues, hydrophilic residues or mixtures thereof; $R_{20-27}$ is a substantially hydrophobic region and $R_{29-31}$ is a substantially hydrophilic region.

2. A peptide of claim 1 in which $R_{12-19}$ is further adapted to a turn in the tertiary structure of the peptide.

3. A peptide of claim 1 in which $R_1$, $R_3$, $R_{7-11}$, $R_{19-22}$ and $R_{25}$ represents hydrophobic amino acid residues; $R_2$, $R_5$, $R_{24}$ and $R_{31}$ represent basic amino acid residues; $R_4$, $R_{26-27}$ and $R_{30}$ represent uncharged hydrophilic amino acid residues; and $R_{12-19}$ represents a region containing hydrophobic residues, hydrophobic residues or mixtures thereof.

4. A peptide of claim 3 in which $R_4$ and $R_{27}$ are asparagine residues and $R_7$ and $R_{21}$ are phenylalanine residues.

5. A serine protease inhibitor peptide consisting of the structure:

$R_{1-5}$-Pro-$R_{7-11}$ in which each R is a naturally occurring amino acid residue or synthetic analog thereof; $R_{1-5}$ is a substantially hydrophilic region and $R_{7-11}$ is a substantially hydrophobic region.

6. A peptide of claim 5 in which $R_1$, $R_3$ and $R_{7-11}$ represent hydrophobic amino acid residues; $R_2$ and $R_5$ represent basic amino acid residues; and $R_4$ represents an uncharged hydrophilic amino acid residue.

7. A peptide of claim 6 in which $R_4$ is an asparagine residue and $R_7$ is a phenylalanine residue.

8. A pharmaceutical composition for inhibiting a serine protease containing an effective amount of a peptide of claim 1 or a nontoxic salt thereof and a pharmaceutically acceptable carrier therefor.

9. A composition of claim 8 in which amino acid residues $R_{12-19}$ provide a turn in the tertiary structure of the peptide.

10. A composition of claim 8 in which $R_1$, $R_3$, $R_{7-11}$, $R_{19-22}$ and $R_{25}$ represent hydrophobic amino acid residues; $R_2$, $R_5$, $R_{24}$ and $R_{31}$ represent basic amino acid residues; $R_4$, $R_{26-27}$ and $R_{30}$ represent uncharged hydrophilic amino acid residues; and $R_{12-19}$ represents a region containing hydrophobic residues, hydrophilic residues or mixtures thereof.

11. A composition of claim 10 in which $R_4$ and $R_{27}$ are asparagine residues and $R_7$ and $R_{21}$ are phenylalanine residues.

12. A pharmaceutical composition for inhibiting a serine protease containing an effective amount of a peptide of claim 5 or a nontoxic salt thereof and a pharmaceutically acceptable carrier therefor.

13. A composition of claim 12 in which $R_1$, $R_3$ and $R_{7-11}$ represent hydrophobic amino acid residues; $R_2$ and $R_5$ represent basic amino acid residues; and $R_4$ represents an uncharged hydrophilic amino acid residue.

14. A composition of claim 13 in which $R_4$ is an asparagine residue and $R_7$ is a phenylalanine residue.

15. A method of treating an individual having a physiological condition caused, in whole or part, by uncontrolled serine protease activity which comprises administering to the individual a therapeutically effective amount of a peptide of claim 1.

16. A method of claim 15 which comprises administering a peptide in which $R_{12-19}$ provides a turn in the tertiary structure of the peptide.

17. A method of claim 15 which comprises administering a peptide in which $R_1$, $R_3$, $R_{7-11}$, $R_{19-22}$ and $R_{25}$ represent hydrophobic amino acid residues; $R_2$, $R_5$, $R_{24}$ and $R_{31}$ represent basic amino acid residues; $R_4$, $R_{26-27}$ and $R_{30}$ represent uncharged hydrophilic amino acid residues; and $R_{12-19}$ represents a region containing hydrophobic residues, hydrophilic residues or mixture thereof.

18. A method of claim 17 which comprises administering a peptide in which $R_4$ and $R_{27}$ are asparagine residues and $R_7$ and $R_{21}$ are phenylalanine residues.

19. A method for treating an individual having a physiological condition caused, in whole or part, by uncontrolled serine protease activity which comprises administering to the individual a therapeutically effective amount of a peptide of claim 5.

20. A method of claim 19 which comprises administering a peptide in which $R_1$, $R_3$ and $R_{7-11}$ represent hydrophobic amino acid residues; $R_2$ and $R_5$ represent basic amino acid residues; and $R_4$ represents an uncharged hydrophilic amino acid residue.

21. A method of claim 20 which comprises administering a peptide in which $R_4$ is an asparagine residue and $R_7$ is a phenylalanine residue.

22. A peptide selected from the group consisting of:

val—lys—phe—asn—lys—pro—phe—val—phe—leu—ile,
val—lys—phe—lys—asn—pro—phe—val—phe—leu—ile,
phe—lys—ala—asn—arg—pro—phe—leu—val—phe—ile, and
val—arg—phe—asn—arg—pro—phe—leu—leu—ile—ile.

23. A peptide selected from the group consisting of:

pro—pro—glu—val—lys—phe—asn—lys—pro—phe—val—phe—leu—ile, pro—asn—arg—val—thr—phe—lys—ala—asn—arg—pro—phe—leu—val—phe—ile,ile—val—arg—phe—asn—arg—pro—phe—leu—leu—ile—ile, phe—leu—glu—ala—ile—pro—met—ser—ile—pro—pro—glu—val—lys—phe—asn—lys—pro—phe—val—phe—leu—ile,ile—ala—gly—arg—ser—leu—asn—pro—asn—pro—pro—glu—val—lys—phe—lys—asn—pro—phe—val—phe—leu—ile,thr—leu—leu—ser—ala—leu—val—glu—thr—pro—pro—glu—val—lys—phe—lys—asn—pro—phe—val—phe—leu—ile,ala—gly—arg—ser—leu—asn—pro—asn—arg—val—thr—phe—lys—ala—asn—arg—pro—phe—leu—val—phe—ile,phe—leu—glu—ala—ile—pro—met—ser—ile—pro—pro—thr—phe—lys—ala—asn—arg—pro—phe—leu—val—phe—ile,thr—leu—leu—ser—ala—leu—val—glu—thr—arg—val—thr—phe—lys—ala—asn—arg—pro—phe—leu—val—phe—ile,thr—leu—leu—ser—ala—leu—val—glu—thr—arg—thr—ile—val—arg—phe—asn—arg—pro—phe—leu—leu—ile—ile,ala—gly—arg—ser—leu—asn—pro—asn—arg—thr—ile—val—arg—phe—asn—arg—pro—phe—leu—leu—ile—ile, phe—leu—glu—ala—ile—pro—met—ser—ile—arg—thr—ile—val—arg—phe—asn—arg—pro—phe—leu—leu—ile—ile,gly—val—arg—gly—pro—arg—val—val—glu—arg—val—thr—phe—lys—ala—asn—arg—pro—phe—leu—val—phe—ile,leu—gln—arg—ala—leu—glu—ile—leu—arg—val—thr—phe—lys—ala—asn—arg—pro—phe—leu—val—phe—ile,ser—pro—phe—arg—ser—val—gln—val—met—arg—val—thr—phe—lys—ala—asn—arg—pro—phe—leu—val—phe—ile,arg—pro—pro—gly—phe—ser—pro—phe—arg—val—thr—phe—lys—ala—asn—arg—pro—phe—leu—val—phe—ile,ile—asp—gly—arg—ile—val—glu—gly—ser—arg—val—thr—phe—lys—ala—asn—arg—pro—phe—leu—val—phe—ile,phe—leu—glu—ala—ile—pro—met—ser—ile—pro—pro—ile—val—arg—phe—asn—arg—pro—

-continued phe—leu—leu—ile—ile,val—lys—phe—asn—lys—pro—phe—val—phe—leu—leu—ile—glu—gln—asn—thr—lys—ser—pro—leu—phe—leu—gly—lys—val—val—asn—pro—thr—gln—lys,arg—val—thr—phe—lys—ala—asn—arg—pro—phe—leu—val—phe—ile—arg—glu—val—pro—leu—asn—thr—ile—ile—phe—leu—gly—arg—val—ala—asn—pro,ile—val—arg—phe—asn—arg—pro—phe—leu—leu—ile—ile—val—pro—thr—asp—thr—gln—asn—ile—phe—phe—leu—ser—lys—val—thr—asn—pro—ser—lys—pro—arg,leu—arg—tyr—asn—lys—pro—phe—ile—leu—val—leu—phe—glu—thr—pro—gly—asn—ser—leu—val—phe—leu—gly—arg—ile—ser—asn—pro—ala—thr—lys,phe—leu—glu—ala—ile—pro—met—ser—ile—pro—pro—glu—val—lys—phe—asn—lys—pro—phe—val—phe—leu—leu—ile—glu—gln—asn—thr—lys—ser—pro—leu—phe—leu—gly—lys—val—val—asn—pro—thr—gln—lys,ile—ala—gly—arg—ser—leu—asn—pro—asn—arg—val—thr—val—lys—phe—asn—lys—pro—phe—val—phe—leu—leu—ile—glu—gln—asn—thr—lys—ser—pro—leu—phe—leu—gly—lys—val—val—asn—pro—thr—gln—lys,thr—leu—leu—ser—ala—leu—val—glu—thr—arg—thr—ile—val—lys—phe—asn—lys—pro—phe—val—phe—leu—leu—ile—glu—gln—asn—thr—lys—ser—pro—leu—phe—leu—gly—lys—val—val—asn—pro—thr—gln—lys,ala—gly—arg—ser—leu—asn—pro—asn—arg—val—thr—phe—lys—ala—asn—arg—pro—phe—leu—val—phe—ile—arg—glu—val—pro—leu—asn—thr—ile—ile—phe—leu—gly—arg—val—ala—asn—pro,phe—leu—glu—ala—ile—pro—met—ser—ile—pro—pro—arg—val—thr—phe—lys—ala—asn—arg—pro—phe—leu—val—phe—ile—arg—glu—val—pro—leu—asn—thr—ile—ile—phe—leu—gly—arg—val—ala—asn—pro,thr—leu—leu—ser—ala—leu—val—glu—thr—arg—val—thr—phe—lys—ala—asn—arg—pro—phe—leu—val—phe—ile—arg—glu—val—pro—leu—asn—thr—ile—ile—phe—leu—ser—lys—val—ala—asn—pro,thr—leu—leu—ser—ala—leu—val—glu—thr—arg—thr—ile—val—arg—phe—asn—arg—pro—phe—leu—leu—ile—ile—val—pro—thr—asp—thr—gln—asn—ile—phe—phe—leu—ser—lys—val—thr—asn—pro—ser—lys—pro—arg,ile—ala—gly—arg—ser—leu—asn—pro—asn—ile—val—arg—phe—asn—arg—pro—phe—leu—leu—ile—ile—val—pro—thr—asp—thr—gln—asn—ile—phe—phe—leu—ser—lys—val—thr—asn—pro—ser—lys—pro—arg,phe—leu—glu—ala—ile—pro—met—ser—ile—pro—pro—ile—val—arg—phe—asn—arg—pro—phe—leu—leu—ile—ile—val—pro—thr—asp—thr—gln—asn—ile—phe—phe—leu—ser—lys—val—thr—asn—pro—ser—lys—pro—arg,ile—ala—gly—arg—ser—leu—asn—pro—asn—arg—val—thr—leu—arg—tyr—asn—lys—pro—phe—ile—leu—val—leu—phe—glu—thr—pro—gly—asn—ser—leu—val—phe—leu—gly—arg—ile—ser—asn—pro—ala—thr—lys,gly—val—arg—gly—pro—arg—arg—ile—ser—asn—pro—ala—thr—lys,gly—val—arg—gly—pro—arg—val—val—glu—arg—val—thr—phe—lys—ala—asn—arg—pro—phe—leu—val—phe—ile—arg—glu—val—pro—leu—asn—thr—ile—ile—phe—leu—gly—arg—val—ala—asn—pro,leu—gln—arg—ala—leu—glu—ile—leu—arg—val—thr—phe—lys—ala—asn—arg—pro—phe—leu—val—phe—ile—arg—glu—val—pro—leu—asn—thr—ile—ile—phe—leu—gly—arg—val—ala—asn—pro,glu—ala—gly—val—asp—ala—ala—ser—val—ser—glu—glu—phe—arg—ala—asp—his—pro—phe—leu—phe—cys—ile—lys—his—ile—ala—thr—asn—ala—val—leu—phe—phe—gly—arg—cys—val—ser—pro,arg—pro—phe—leu—val—phe—ile—arg—glu—val—pro—leu—asn—thr—ile—ile—phe—leu—gly—arg—val—ala—asn—pro,arg—pro—phe—leu—val—phe—ile—leu—pro—gly—ile—phe—leu—gly—arg—val—ala—asn—pro,arg—pro—phe—leu—val—phe—ile—leu—pro—asn—ile—phe—leu—gly—arg—val—ala—asn—pro,arg—pro—phe—leu—val—phe—ile—arg—pro—gly—asp—ile—phe—leu—gly—arg—val—ala—asn—pro,arg—pro—phe—leu—val—phe—ile—arg—pro—asn—asp—phe—leu—gly—arg—val—ala—asn—pro,arg—pro—phe—leu—val—phe—ile—leu—pro—asn—ile—phe—leu—gly—arg—val—ala—asn,pro—phe—leu—val—phe—ile—leu—pro—asn—ile—phe—leu—gly—arg—val—ala—asn,arg—pro—phe—leu—val—phe—ile—leu—pro—asn—ile—phe—leu—arg—val—ala—asn—pro,ile—ala—gly—arg—ser—leu—asn—pro—asn—arg—val—thr—phe—lys—ala—asn—arg—pro—phe—cys—val—phe—ile—arg—glu—val—pro—leu—asn—thr—ile—ile—phe—leu—gly—cys—val—ala—asn—pro—ala—val—lys,arg—pro—phe—leu—val—phe—leu—pro—asn—ile—leu—arg—val—ala—asn—pro,lys—ala—pro—gly—arg—val—val—gly—gly—ala—val—arg—val—thr—val—lys—phe—asn—lys—pro—phe—val—phe—leu—leu—ile—glu—gln—asn—thr—lys—ser—pro—leu—phe—leu—gly—lys—val—val—asn—pro—thr—gly—lys,glu—ile—ile—leu—pro—arg—pro—phe—leu—phe—val—val—arg—his—asn—pro—thr—ser—thr—val—leu—phe—leu—gly—gln—val—leu—glu—pro,ala—val—ile—val—ser—ala—arg—met—ala—pro—glu—ile—ile—leu—pro—arg—pro—phe—leu—phe—val—val—arg—his—asn—pro—thr—ser—thr—val—leu—phe—leu—gly—gln—val—leu—glu—pro,val—ala—arg—thr—leu—leu—val—phe—glu—val—gln—arg—val—thr—phe—lys—ala—asn—arg—pro—phe—leu—val—phe—ile—arg—glu—val—pro—leu—asn—thr—ile—ile—phe—leu—gly—arg—val—ala—asn—pro,phe—val—ala—asn—his—pro—phe—leu—phe—leu—ile—arg—glu—asp—ile—ala—gly—val—val—val—phe—val—gly—his—val—thr—asn—pro,ser—met—pro—leu—lys—val—asp—leu—val—asp—phe—val—ala—asn—his—pro—phe—leu—phe—leu—ile—arg—glu—asp—ile—ala—gly—val—val—val—phe—val—gly—his—val—thr—asn—pro—ala—val—lys,arg—val—thr—phe—lys—ala—asn—arg—pro—phe—leu—val—phe—ile—arg—glu—val—pro—leu—asn—thr—ile—ile—phe—leu—gly—arg—val—ala—asn—pro—ala—val—lys,arg—asp—lys—gly—

-continued gln—ala—gly—leu—gln—arg—ala—leu—arg—val—thr—phe—lys—ala—asn—arg—pro—phe—leu—val—phe—ile.and arg—asp—lys—gly—gln—ala—gly—leu—gln—arg—ala—leu—glu—ile—leu—gln—arg—val—thr—phe—lys—ala—asn—arg—pro—phe—leu—val—phe—ile.

24. A peptide selected from the group consisting of:

val—lys—phe—asn—lys—pro—phe—val—phe—leu—leu—ile—glu—gln—asn—thr—lys—ser—pro—leu—phe—leu—gly—lys—val—val—asn—pro—thr—gln—lys.arg—val—thr—phe—lys—ala—asn—arg—pro—phe—leu—val—phe—ile—arg—glu—val—pro—leu—asn—thr—ile—ile—phe—leu—gly—arg—val—ala—asn—pro.ile—val—arg—phe—asn—arg—pro—phe—leu—leu—ile—ile—val—pro—thr—asp—thr—gln—asn—ile—phe—phe—leu—ser—lys—val—thr—asn—pro—ser—lys—pro—arg.leu—arg—tyr—asn—lys—pro—phe—ile—leu—val—leu—phe—glu—thr—pro—gly—asn—ser—leu—val—phe—leu—gly—arg—ile—ser—asn—pro—ala—thr—lys. glu—ala—gly—val—asp—ala—ala—ser—val—ser—glu—glu—phe—arg—ala—asp—his—pro—phe—leu—phe—cys—ile—lys—his—ile—ala—thr—asn—ala—val—leu—phe—phe—gly—arg—cys—val—ser—pro.glu—ile—ile—leu—pro—arg—pro—phe—leu—phe—val—val—arg—his—asn—pro—thr—ser—thr—val—leu—phe—leu—gly—gln—val—leu—glu—pro.and phe—val—ala—asn—his—pro—phe—leu—phe—leu—ile—arg—glu—asp—ile—ala—gly—val—val—val—phe—val—gly—his—val—thr—asn—pro.

25. A peptide of claim 23 of the formula:

ile—ala—gly—arg—ser—leu—asn—pro—asn—arg—val—thr—leu—arg—tyr—asn—lys—pro—phe—ile—leu—val—leu—phe—glu—thr—pro—gly—asn—ser—leu—val—phe—leu—gly—arg—ile—ser—asn—pro—ala—thr—lys.

* * * * *